United States Patent [19]

Specht et al.

[11] 4,271,842
[45] Jun. 9, 1981

[54] APPARATUS AND METHOD FOR PROVIDING MULTIPLE ULTRASONIC SECTOR IMAGE DISPLAYS

[75] Inventors: Donald F. Specht, Mountain View; Paul R. Goldberg, Palo Alto, both of Calif.

[73] Assignee: Smith Kline Instruments, Inc., Sunnyvale, Calif.

[21] Appl. No.: 883,171

[22] Filed: Mar. 3, 1978

[51] Int. Cl.³ .............................................. A61B 10/00
[52] U.S. Cl. ....................................... 128/661; 73/620
[58] Field of Search .......... 128/2 V, 2.05 Z, 660–663; 73/602–603, 618–626; 250/363 S, 445 T; 358/111–113; 364/731, 576–577, 819–821

[56] References Cited

U.S. PATENT DOCUMENTS

| | | | |
|---|---|---|---|
| 3,624,744 | 11/1971 | Munger | 128/2 V |
| 3,744,479 | 7/1973 | Stein et al. | 128/2 V |
| 3,830,223 | 8/1974 | Beretsky et al. | 128/2.05 Z |
| 3,864,660 | 2/1975 | Ronalli et al. | 128/2.05 Z X |
| 3,871,360 | 3/1975 | Van Horn et al. | 128/2.05 R |
| 3,952,201 | 4/1976 | Hounsfield | 250/403 |
| 3,954,098 | 5/1976 | Dick et al. | 128/2.05 Z |
| 3,955,561 | 5/1976 | Eggleton | 128/2.05 Z |
| 3,974,826 | 8/1976 | Eggleton et al. | 128/2 V |
| 4,029,948 | 6/1977 | Hounsfield | 358/111 |
| 4,033,335 | 7/1977 | Nickles | 128/2 A |
| 4,034,744 | 7/1977 | Goldberg | 128/2 V |
| 4,037,585 | 7/1977 | Gildenberg | 128/2 A |
| 4,045,815 | 8/1977 | Griffith et al. | 358/183 |
| 4,058,001 | 11/1977 | Waxman | 128/2 V |
| 4,075,883 | 2/1978 | Glover | 128/2 V |
| 4,079,417 | 3/1978 | Scudder | 358/111 |
| 4,100,916 | 7/1978 | King | 128/661 |
| 4,111,055 | 9/1978 | Skidmore | 128/661 |
| 4,121,250 | 10/1978 | Huelsman | 358/112 X |
| 4,127,034 | 11/1978 | Ledermann et al. | 73/626 |
| 4,159,462 | 6/1979 | Rocha et al. | 738/626 |

OTHER PUBLICATIONS

Vogel, J. A. et al., "Processing Eqpt. for Z-D Echocardiographic Data", UTS in Mode & Biol., vol. 2, pp. 171–179, No. 3, Jun. 1976.

Myrick, R. J. et al., "Real Time Digital Echocardiography Using Burst Analog Sampling", IEEE Trans SIUS vol. Su-24, No. 1, pp. 19–23, Jan. 1977.

Brennecke, R. et al., *Simultaneous Recording of X-Ray TV Pictures and Digital Physiological Measurement Data in the Video Band*, Biomed Technik, vol. 21, (supplement) pp. 33–34, Jun. 1976.

Wood, E. H. *New Horizons for Cardiopulmonary and Circulatory Systems*, Chest, 69:3 Mar. 1976.

Robb, R. A. et al. *3-D Reconstruction and Display of the Working Canine Heart and Lungs by Multi-Planar X-Ray Scanning Videodensitometry*, Proc. Intnl. Wkshp. Brookhaven Natural Lab, Upton N.Y. Jul. 16, 1974 pp. 99–106.

Greenleaf, J. F. et al., *Algeb Reconst of Spatial Dist. of Acoustic Vel. in Tissues from TOF Profiles*, Acoustic Holog. vol. 6, 1975, pp. 71–90.

Namery, J. et al., "*UTS Detection of Myocardial Infarction in Dog*", IEEE SIUS, 1972 pp. 491–494.

Kikuchi, Y. et al. *Ultrasono Cardiotomography*, Jap. Elec. Engr., Oct. 1970, pp. 53–60.

McSherry, D. H. *Computer Processing of Diagnostic Ultrasound Data*, IEEE Trans. on Sonics & Ultrasonics, vol. SU-21, No. 2, Apr. 1974, pp. 91–97.

Smith, R. J. *Bit Slicer Converts Radar Position Coordinates*, Electronics, Apr. 15, 1976, pp. 136–138.

Yokoi, H. et al. *Quantitative Color Ultrasonography by Means of a Computer Aided Simultaneous Tomogram*, Ultrasonics, vol. 13, No. 5, Sep. 1975 pp. 219–224.

Milan, J. et al., *An Improved UTS Scan System Employing a Small Digital Computer*, Brit. Jrnl. Rad., #45, Dec. 1972, pp. 911–916.

*Ultrasound Echoview System 80 L*, Picker Corp., Northford Conn. 06472 (undated) Broch No. PG6435/1175/B349.

Sano, R. M. et al. *A Nuclear Cardiology Module for Anger Cameras*, Picker Corp., Northford Conn, (SNM 24th Ann MTG, Instr z:Poster Session, Jun. 24, 1977.

Albert, N. M. et al, *Non-Invasive Nuclear Kinecardiography*, Jrnl. of Nuclear Med., vol. 15, No. 12, Dec. 1974, pp. 1182–1184.

*Primary Examiner*—Robert W. Michell
*Assistant Examiner*—Francis J. Jaworski
*Attorney, Agent, or Firm*—Flehr, Hohbach, Test

[57] ABSTRACT

The apparatus includes an input controller connected to receive input data representing ultrasonic sector images of a patient for digitizing selected ones of the images thereby representing those images in a digital format. A front panel interface is provided for specifying the selected ones of the sector images to be digitized. Storage means are provided for storing the digitized data and processor means are provided for controlling the digitizing and storing of the input sector data and for enhancing the digital images. Display means are provided for displaying the enhanced sector images.

15 Claims, 5 Drawing Figures

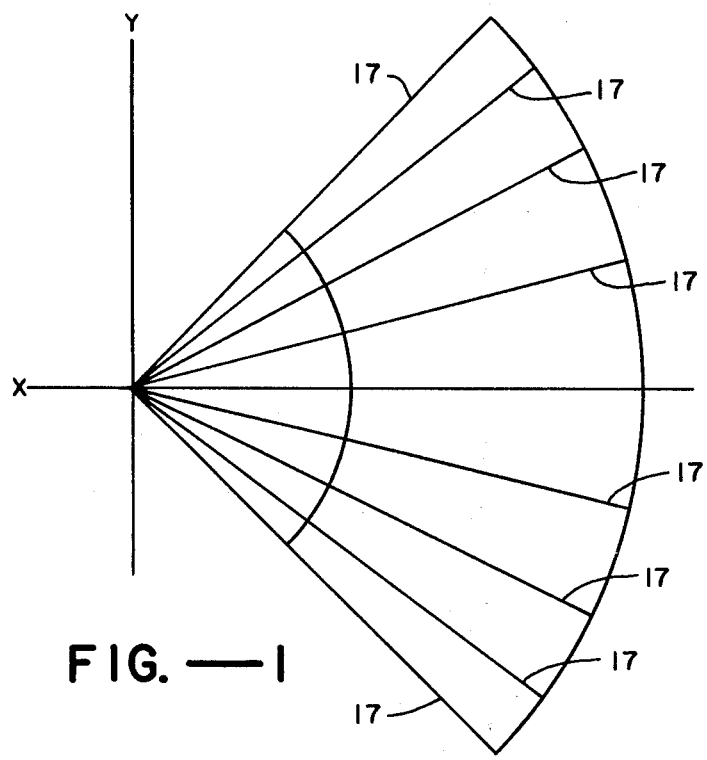
FIG.—1
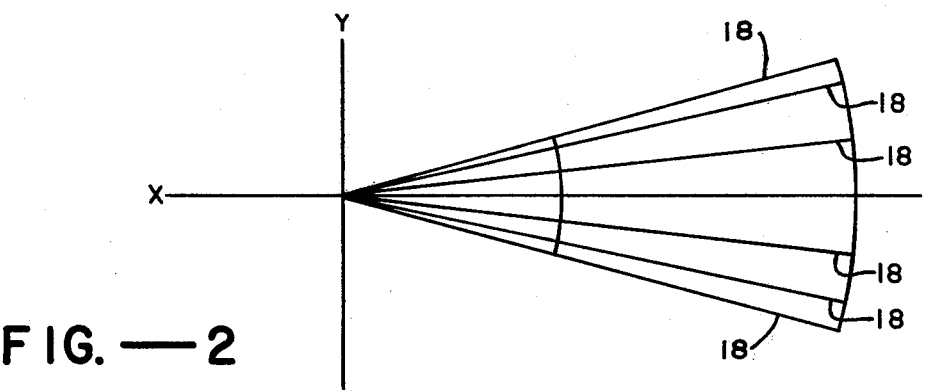
FIG.—2
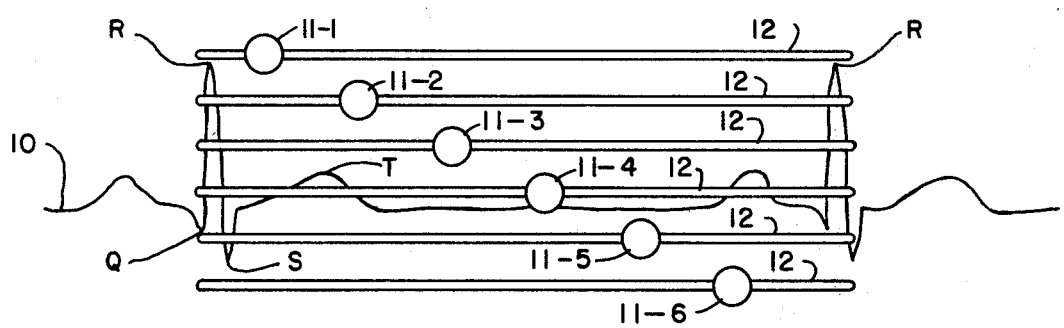
FIG.—3

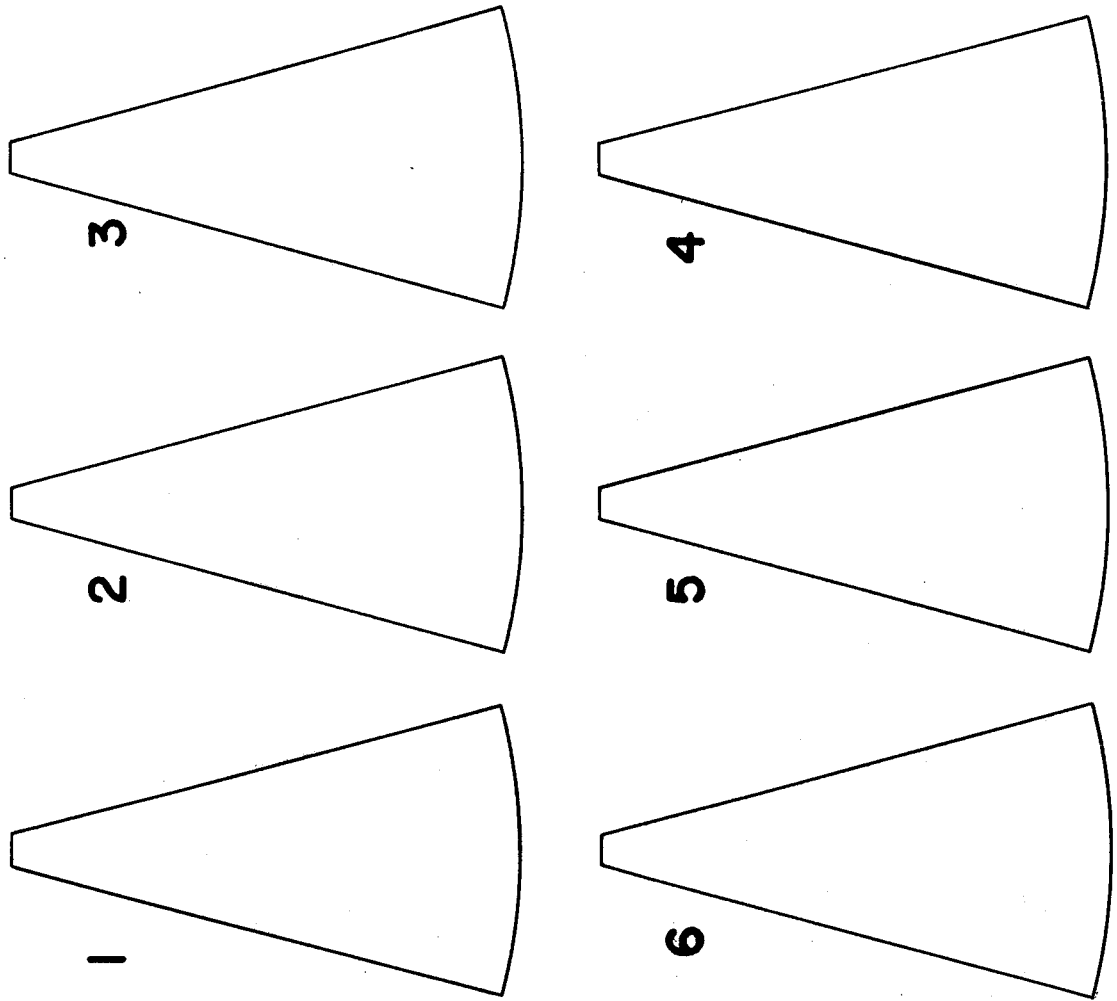
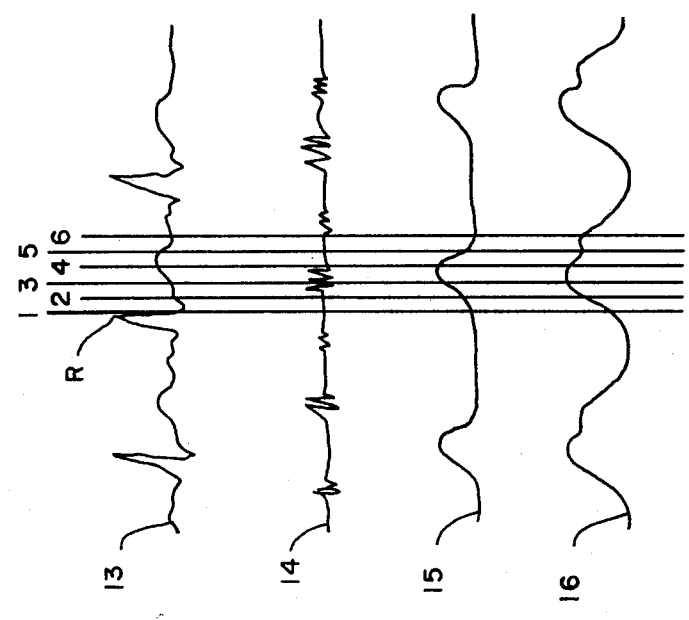
FIG.—4

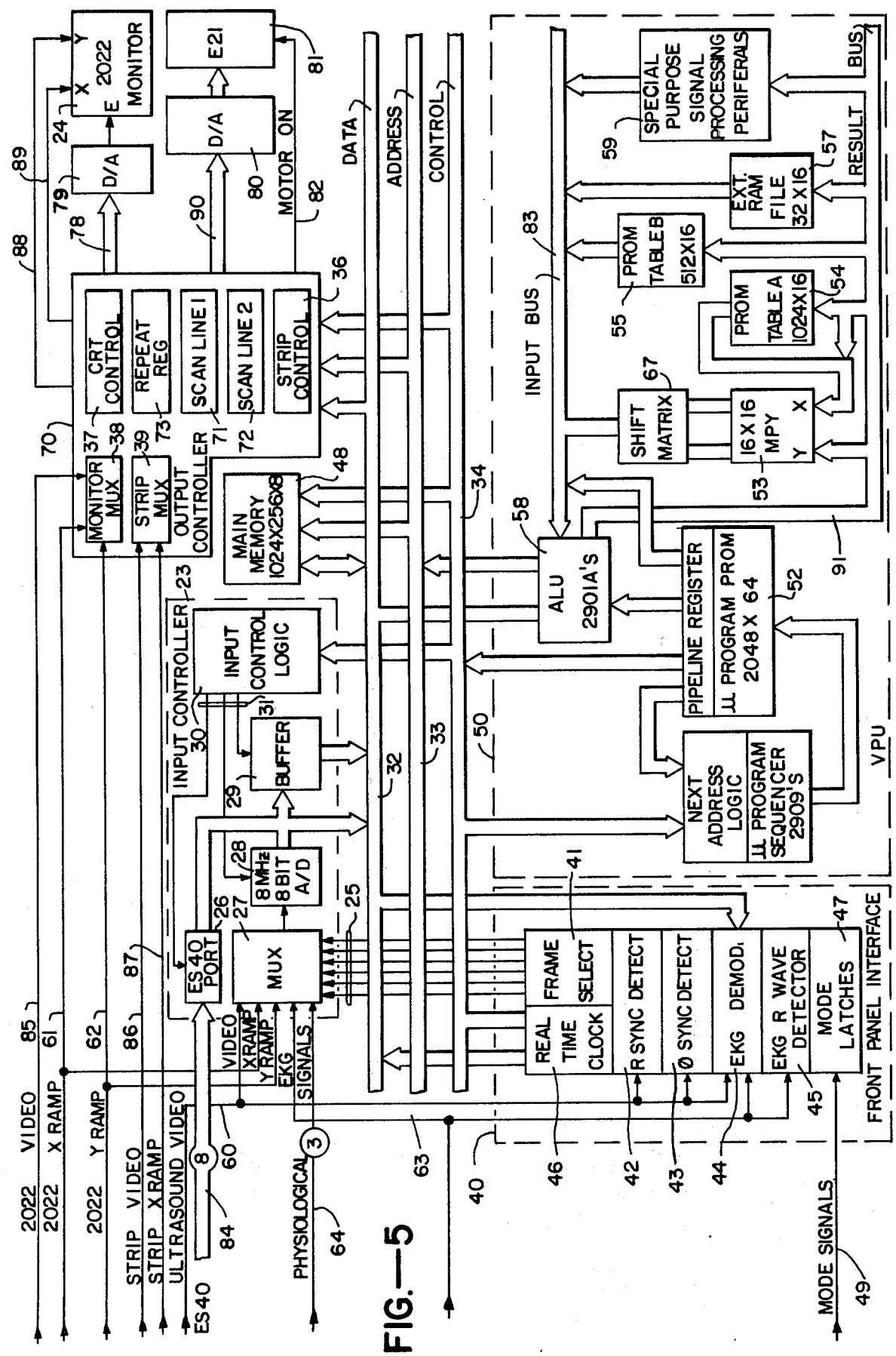
FIG.—5

APPARATUS AND METHOD FOR PROVIDING MULTIPLE ULTRASONIC SECTOR IMAGE DISPLAYS

BACKGROUND OF THE INVENTION

The present invention relates to apparatus providing multiple ultrasonic sector image displays.

Ultrasonic scanning of regions of the human body has found wide application in recent years. A particular type of scanner used is a sector scanner since it has the ability to display a cross-sectional area of the human body. An ultrasonic sector scanner consists of a transducer or transducers and a means of steering the ultrasonic beam through a series of angles. The steering means can be either mechanical (moving the transducer(s)) or electronic (phased arrays) or a combination of the two. The transducer itself can be a single element or an arrangement of many elements which together form a beam. Multiple element transducers include linear phased arrays pulsed in groups, annular phased arrays, and two-dimensional matrix phased arrays.

In the preferred embodiment a mechanical sector scanner is used to produce the signals to be processed. In this scanner an ultrasonic transducer (a piezoelectric element) is mounted and motor driven through a suitable mechanical arrangement. The drive arrangement moves the transducer with an arc scanning motion. During this process, the transducer is pulsed with high voltage spikes at selected pulse repetition rates. The voltage spikes cause the piezoelectric element to mechanically ring thereby emitting very high frequency sound waves. These ultrasonic waves impinge upon the structure within the body, and when a difference of acoustic impedance exists, are partially reflected back to the transducer element. In the interval between pulses, the transducer element acts as a receiver. The reflected energy causes the transducer element to mechanically vibrate and the element generates an electrical signal. This signal is amplified and processed so that it can be displayed as a sector scan on a cathode ray tube.

In one approach, the mechanical driving arrangement not only drives the probe but also provides an electrical output analogous to transducer position by the use of position sensing means such as a potentiometer which translates position information into electrical energy. The electrical signal is processed and utilized to create horizontal and vertical signals which, along with the returning ultrasonic impulses, are used to create an X-Y display on the cathode ray tube. The resultant image is a representation of the internal organs of the body.

Scan displays on the cathode ray tube can be on the order of a 30°, 90° or 120° scan with a plurality of scan lines each beginning with the application of a pulse to the transducer and each field or scan representing the cross section scanned.

In order for the information displayed on the cathode ray tube monitor to be most effective in use, it is necessary to record these images so that they can later be viewed and compared. The scan image appearing on a cathode ray tube in real time is continuously changing, thereby making comparisons between images and/or measurements difficult.

In application to the field of cardiology, a desirable feature of ultrasonic scanning systems would be to provide a simultaneous display of successive frames of sector data acquired during the same cardiac cycle—for instance, the sector images occurring during early diastole, mid-diastole, late diastole, early systole, mid-systole, late systole.

One prior art approach for recording a sector image is to use an instant camera, which obviates the possibility of recording consecutive sector images (unless a multiframe camera is used). Another approach has been to use a movie camera or video tape recorder which provides closely spaced pictures.

In other prior art approaches, a strip chart recorder provides in hard copy form a readout of what is known as an intensity-modulated M-mode display. The recorder records on strip chart paper ultrasonic echo information as a function of time. Such strip chart readouts are particularly valuable in the study of motion patterns of moving structures within the heart.

It is desirable to provide apparatus for printing multiple sector images in hard copy form, such as those sector images occurring during one cardiac cycle, so that the attending physician can have at hand a "cardiac image profile" of sector data. Prior art systems have not had the capability of providing a hard copy of multiple sector scans taken closely spaced in time. Additionally, it is desirable to provide apparatus for displaying physiological parameters such as the electrocardiogram, phonocardiogram, blood pressure and pulse to further assist a physician in his anaylsis.

It would also be desirable to provide apparatus that could provide particular sector image displays on a cathode ray tube—a soft copy form of the display—thereby giving an attending physician the choice of selecting which images to output to the hard copy device.

Additionally, it would be desirable to incorporate digital techniques to enhance the sector image. One problem in the prior art occurs with the displaying of the scan lines themselves on a cathode ray tube along with the desired image information.

The appearance of the scan lines distracts the physician from the real information content of the image. A desirable objective would be to provide a digital processor which eliminates the appearance of noticeable scan lines.

In view of the above background, it is an object of the present invention to provide enhanced multiple-sector hard copy images of the heart and other body organs.

SUMMARY AND OBJECTS OF THE INVENTION

The present invention relates to apparatus for providing multiple sector image displays in hard copy or soft copy form.

In one embodiment, the apparatus provides multiple sector image displays synchronized relative to a predetermined point along a patient's physiological event such as the occurrence of the R-wave from an electrocardiogram waveform. The apparatus includes means for specifying selected ones of the sector images relative to the predetermined point. However, the apparatus does not require a physiological event for proper operation. For example, the apparatus could be continuously sampling input data without relying upon physiological event.

The apparatus also includes an input controller for digitizing input data representing sector images of a patient occurring during one or more cardiac cycles. Storage means are included for storing the digitized data and processor means are provided for controlling the digitizing and storing of the sector data and for enhancing the digitized images. Display means are provided for displaying the enhanced data thereby representing one or more sector images. The display means could be a strip chart recorder or any other hard copy recorder for displaying the sector images in hard copy form, or a cathode ray tube display for displaying the sector images in soft copy form, or both. In a preferred embodiment, the hard copy is displayed on the same strip chart recorder commonly used for M-mode studies (for economical reasons). However, the image could be reproduced photographically or electrostatically just as well.

In accordance with the above summary, the present invention achieves the objective of providing enhanced sector images of the heart and other body organs.

It is another objective of the present invention to allow recording of high quality sector images to be displayed simultaneously with a patient's physiological parameters such as EKG, pulse, phonocardiogram, blood pressure or other parameters. The dimensional accuracy should be sufficient that numerical measurements needed for diagnosis can be scaled from the hard copy output.

These and other objects and features of the invention will become apparent from the following detailed description when taken in conjunction with the accompanying drawings.

BRIEF DESCRIPTION OF THE DRAWINGS

FIG. 1 depicts a sector image appearing on a cathode ray tube for a wide angle probe.

FIG. 2 depicts a sector image appearing on a cathode ray tube for a 30° probe.

FIG. 3 depicts a portion of a front panel of one embodiment of the present invention for selecting specified sector images synchronized to the R-wave detection of a patient's electrocardiogram waveform.

FIG. 4 depicts physiological parameter waveforms and sector images printed on strip chart paper in accordance with the present invention.

FIG. 5 depicts a block diagram representation of one embodiment of the present invention.

DETAILED DESCRIPTION OF THE DRAWINGS

Referring to FIGS. 1 and 2, typical sector images provided by prior art apparatus are depicted for a wide angle probe and for a 30° probe, respectively. As previously described, the techniques of producing sector images such as in FIGS. 1 and 2 are well known in the art. One particular system for forming a sector display is shown and described in U.S. Pat. No. 4,034,744. The images of FIGS. 1 and 2 are formed on scan lines 17, 18 respectively, which represent the direction of the reflected ultrasonic energy. The image is formed by controlling the intensity of the display along the lines to show the intensity of the reflected energy.

In one embodiment of the present invention, the selection of the sectors is synchronized to a patient's electrocardiogram (EKG). Waveform 10 as depicted in FIG. 3 is a typical EKG inscribed on the front panel as an aid to a physician in setting the selection knobs 11. The sectors are selected by controls on front panel such as illustrated in FIG. 3. The controls are typically slide potentiometers for selecting the six sectors to be displayed relative to R-wave detection. Selection knobs 11 are slidably adjustable along frame selection rods 12 for selecting the desired sector images in terms of percentage delay from one R-wave detection to the next. However, it is to be understood that the apparatus is not dependent upon a patient's physiological event such as an EKG waveform. The apparatus, for example, could be continuously sampling input data without reliance upon a patient's physiological event.

The repetitive EKG waveform 10 includes P, Q, R, S and T waves which occur during a typical cardiac cycle. The occurrence of the R-wave, which is a highly positive pulse compared to the P, Q, S and T waves, is a convenient synchronization point for initiating selection of sector images to be displayed.

In one embodiment of the invention, up to six different sector images can be displayed; however, conceptually any number of sector images can be chosen, depending upon hardware restriction requirements. In order to provide multiple sector displays in hard or soft copy form, the apparatus must be capable of storing input data representing the sector images because multiple sectors presently cannot economically be enhanced and displayed in real time.

Referring now to FIG. 4, there is shown a representation of one type of printout in accordance with the present invention. In this embodiment of the invention a strip chart recorder is utilized for displaying the sectors. A patient's name and I.D. number together with the date and time can be displayed on the strip chart paper. Physiological parameters which can be displayed on the strip chart paper are the EKG 13, phonocardiogram 14, pulse 15 and blood pressure 16. Other parameters can be displayed instead of these or in addition as desired.

In FIG. 4, the sector selection positions 1-6 are shown with sector 1 shown occurring at R-wave detection and sectors 2-6 sequentially occurring thereafter. The selected sectors can be any sector images occurring during the cardiac cycle between successive R-wave detections.

In FIG. 4, a transition display of sector images in hard copy form is shown with six sector respresentations depicted. The sector displays are numbered sequentially in clockwise direction from sector 1-2-3-4-5-6-1 and correspond to the sector selection positions shown on EKG waveform 13. The transition display provides easier comparison for successive cardiac sector images. For example, sector 3 is easily compared with sector 4, sector 4 with sector 5, sector 6 with sector 1. A physician is thereby provided with a "cardiac image profile" during one cardiac cycle.

Referring now to FIG. 5, a block diagram depicting one embodiment of the present invention is shown. Input data can be from a video tape recorder in which the analog data has previously been recorded or from ultrasonic units such as SKI's Model EkoSector I (ESI) or Model EkoSector 40 (ES40) which provide analog data. Analog data from an EKG device, and other signals to be described, are also input. An input controller 23 receives the input data representing sector images of a patient for digitizing ones of the sector images thereby representing the images in a digital format. A front panel interface 40 includes a frame select 41 for specifying the particular sector images to be digitized. The digitized data is stored in memory 48. A video processing unit (VPU) 50 controls the digitizing and storing of the input sector data and enhances the digital images by a computation portion of the system microcode. An output controller 70 is connected to receive the enhanced data from the video processing unit 50 for converting the enhanced data to an analog format for connection to a strip chart recorder 81 which displays the multiple sector images of the patient.

Ultrasonic video data on bus 60 from either an ESI or ES40 is input to multiplexer (MUX) 27 and into the front panel interface 40. Data for display on a typical CRT monitor 24 such as Wavetek's Model 2022 is input on bus 85, together with X-Ramp and Y-Ramp data on buses 61, 62. Data on buses 61, 62, 85 are connected to monitor multiplexer 38 in output controller 70 where, under control of typical CRT control circuit 37, video data can be displayed on monitor 24, as will be described. Physiological data on bus 64 from a typical set of biomedical preamplifiers may include signals such as phonocardiogram, blood pressure and pulse.

The strip chart multiplexer 39 in the output controller 70 is used to select between the input strip chart data on bus 86 (which is M-mode) or the data generated by the VPU 50, scan line buffers 71 and 72, and the D/A converter 80. The data is under control of strip chart control circuit 36 and connected to a strip chart recorder 81 such as SKI Model E21 or a dry silver paper recorder.

An 8-bit communications channel 84 is input to port 26 in input controller 23 because a unit such as SKI Model ES40 can transfer parameter and patient I.D. information in digital format directly to the input controller 23 rather than requiring digitizing of that data.

Mode signals on bus 49 from a unit such as SKI's Model ESI are input to mode latch unit 47 in front panel interface 40 to specify M-mode or sector mode operation.

Data input to controller 23 is in the form of ultrasound video data on bus 60, X-Ramp data on bus 61, Y-Ramp data on bus 62, EKG data on bus 63 and other physiological data on bus 64. The data on buses 60-64 are input to multiplexer 27 in controller 23, which also includes an analog to digital converter 28, FIFO buffer 29 and input control logic 30, which provides appropriate control signals on bus 31. In one embodiment, the analog/digital converter 28 is an 8 MHz 8-bit converter. The data actually needs to be digitized only to 3-4 bits resolution if it were to be displayed directly, but for image enhancement purposes is digitized to 8 bits per sample by converter 28.

The multiplexer 27 switches/multiplexes the appropriate input signals to the digitizer 28 under program control. Selection of particular sectors are selected by frame select 41, which corresponds to the sector selection depicted in FIG. 3.

In FIG. 5, interface 40 also includes an R-sync detect circuit 42 and $\theta$-sync detect circuit 43, which indicates to the processor the beginning of each scan line and field respectively.

The EKG demodulator 44 of interface 40 is utilized for picking off a pure electrocardiogram waveform from the video format. The R-wave detector 45 provides a signal indicating when each R-wave of the electrocardiogram has been detected.

In FIG. 5, the main memory 48 is a 1024×256×8-bit memory for storing the digitized data under control of the video processing unit (VPU) 50 via data bus 32. One feature of this memory is that it is organized by row and column just as is the image data to be processed. This organization speeds accessing in image processing applications.

The VPU 50 controls the operation of the system via data bus 32, address bus 33, and control bus 34, and includes in one embodiment the AMD 2900 series of bit-sliced microprocessors. VPU 50 is a general purpose 16-bit processor with features such as addressing main memory 48 by row and column rather than standard linear organization.

The pipeling register and microprogram PROM 52 stores the system microcode, which in the present embodiment is a series fo instructions incorporating 64-bit microcontrol words. The system microcode for one mode of operation of the system is included in Appendix I. The example provided in Appendix I uses the SKI 30° probe and the EkoSector I as input devices, the Ekoline 21 as the output device, and the algorithm is set to capture a "cardiac profile" as described above.

The algorithms for implementing the operation of the system involve a large number of fixed point multiplications, and therefore a high-speed 16×16 bit multiplier 53 is utilized (such as TRW Model MPY-16).

The shift matrix 67 in FIG. 5 is utilized for dividing by any powers of two up to $2^{15}$. The multiplier-shifter can be utilized for multiplying fixed point quantities by a fractional quantity.

In FIG. 5, the PROMs 54, 55 store constants used in manipulating the operation of the digitized data. External RAM file 57 is a 32×16 bit register for increasing the number of general purpose registers in the system to forty-eight. The arithmetic and logic unit 58, which communicates with the other units via 16-bit input bus 83 and 16-bit result bus 91, contains sixteen general purpose registers which together with the thirty-two registers in RAM file 57 form the forty-eight general purpose registers. ALU 58 could be based on the AMD 2900 series bit-sliced microprocessor chips.

In addition to eliminating the scan lines, the digital processor can enhance the image in a number of other ways. One of these ways is through deconvolution techniques. In a preferred embodiment, only the lateral resolution is enhanced because lateral resolution is inherently poorer than radial resolution. In that embodiment, each lateral arc is Fourier transformed (using a fast Fourier transform algorithm), multiplied by an appodized version of the inverse of the modulation transfer function and inverse transformed back to the spatial domain. The same deconvolution could be performed equivalently by convolution of the original data with an appropriate inverse function entirely in the spatial domain. Also, a wide variety of approximation algorithms could be applied to improve the shape of the effective point spread function.

In application to scanners applied to areas of the body other than the heart, some, but not all, of the elements of this invention are effective. Although timing relative to cardiac events is no longer useful, it is still important in these cases to acquire a frame of data in a short time (to freeze motion), to digitally remove the appearance of scan lines, to improve the resolution through deconvolution techniques, to preview the image on the CRT and to output the enhanced image on a hard copy device if desired. Deconvolution techniques are utilized because input sector data is invariably degraded by the less than ideal beam spread function. Expressed otherwise, the degradation results from convolution of the desired image with the point spread function of the transducer.

In FIG. 5, the output controller 70 contains two 1024×4 bit scan line buffers 71, 72 for storing data from the VPU 50 and main memory 48. Data is written into one buffer while data is read out of the other buffer. The data is read out of buffer 71 or 72 using repeat counter 73. The output controller 70 reads out each scan line four times from the designated buffer 71 or 72 in order to make the lines recorded by the recorder 81 so closely spaced that they are not easily discernable. The output from controller 70 in input to conventional D/A converter 80 and strip chart recorder 81, where it is displayed on strip chart paper. Another recorder that could be utilized is an electrostatic printer/plotter (such as Versatec's) which can accept digital data directly, thereby eliminating the need for converting data to an analog format.

CRT control 37 provides X and Y control data for monitor 24. Control 37 also controls the 4-bit data on bus 78 to digital to analog converter 79 to provide video on monitor 24.

One format of the printout to be presented after data capture and conversion is one in which all six frames of data are printed out two at a time with each sector being approximately 8.7 cm deep by 5 cm (30° probe) as in FIG. 4, or 13.8 cm (wide angle probe) wide. The user can, by an appropriate front panel control selection (not shown), cause any sector to be expanded to double size.

In one embodiment, a user can pick systole or any other event defined as a time delay after R-wave detection in succeeding heart cycles, or obtain a "cardiac image profile" over a single cycle such as early diastole, mid-diastole, late diastole, early systole, mid-systole, and late systole.

The system can acquire data in real time directly from an ultrasonascope, or from a video tape recorder.

The system has digital storage for six frames of ultrasound data where each picture element is represented by 8 bits to maintain sufficient resolution for subsequent digital image enhancement. Any of the six stored and enhanced frames can be instantly viewed in any order on the monitor 24 as determined from selection switches on the front panel. After previewing, any image or all six images can be printed on the video strip chart recorder 81.

The VPU 50 is used to interpolate between data points to provide high quality, high line density sector images. In one embodiment, up to four physiological parameters are displayed on the same hard copy output as the sector images, as depicted in FIG. 4. Sector images synchronized with various points on the EKG waveform are written on a record which also displays the accompanying EKG, pulse phonocardiogram and blood pressure. Also, a patient's identification number, date and time of day are printed out as depicted in FIG. 4.

The output format as depicted in FIG. 4 is for a 30° sector. The format for a wide angle sector is similar but requires a strip of paper approximately twice as long. These formats are chosen so that a 30° record could be a single sheet of paper the size of which is easily inserted into a patient's folder. The wide angle record is folded in the center to fit in a standard-sized patient's folder.

The storage modes for displaying the sectors are as follows:

In a storage strobe control mode, the system utilizes one frame from each cardiac cycle selected. The frame, updated once per cardiac cycle, is refreshed on monitor 24. In this storage mode, the system has two submodes. In one submode, the system stores each strobed frame until the operator hits a foot switch (not shown). This leaves the last six strobed frames in storage. In the other submode, the system stores each strobed frame plus the three before and two after until the operator hits the foot switch, leaving a cluster of six strobe frame "centered" around the last strobed frame in storage.

The system utilizes one of the six slide potentiometers shown in FIG. 3 to determine which frame in the cardiac cycle is to be used to update the frame storage. The selection of which one of the slide potentiometers is active for this purpose is made from a numeric keyboard on the front panel (not shown). Strobe mode can be used to stop the motion of the image. By operating the slide potentiometer of FIG. 3, the physician can move slowly in time relative to the R-wave, either forward or in reverse.

The above described strobe mode is intended to be used only with a device such as SKI's Model EkoSector I, which does not have a strobe mode capability. Other devices, such as SKI's EkoSector 40 1 (ES40) which is presently being designed will have this strobe mode design as an integral part of the unit. When the system is operating with the ES40, the ES40 will send the system a synchronizing bit to indicate on which frame it is strobing. The system would have the same two storage modes as described above, but the image displayed on the monitor prior to the operator hitting the foot switch would be that generated by the ES40.

Another mode is to store a cluster in real time, in which the system keeps a rolling record of the last six frames. The operator, upon seeing an interesting occurrence on the real time monitor 24, can hit the foot switch and store the last six frame (approximately 200 msec of data). This mode can be used to compensate for the reaction time of a physician. After freezing the last six frames, he can then review them to find the one he was looking at when he hit the switch, which could be printed on hard copy.

Another mode is programmable sampling system, in which the user obtains the "cardiac image profile" over a single cycle, e.g., early diastole, mid-diastole, late diastole, early systole, mid-systole, late systole.

The physician selects the cardiac cycles to be output in hard copy form by observing the CRT display and activating a foot switch (not shown). It is important to display on paper the data which has appeared on the screen. The alternative, saving a cycle commencing at a particular part of the cycle unrelated to the time of foot switch actuation, would require that some of the sectors saved occur after foot switch actuation. Therefore, the device keeps a rolling record. As each specified frame occurs, it replaces the equivalent frame from the previous cardiac cycle. When the physician actuates the foot switch, this indicates that the system should stop updating frames, which can then be printed out in hard copy form if desired. Depending on where in the cycle the foot switch was actuated, the latest data saved may correspond to the time selected by any one of the six sector position selection controls. The image that the physician has spent time finding using the strobe mode should be one of the six stored. Therefore, the strobed image will take the place of the closest one of the six images selected by the slide pots of FIG. 3. This is true whether the CRT viewing mode is strobe or real time.

Approximately one second after the six stored frames are frozen by any of the storage modes described above, one of the six images is enhanced and then displayed on the monitor 24. In one display mode, the image displayed is the last strobed image. In a strobe mode with a unit such as the ES40, the image displayed is replaced by the enhanced image when it becomes available. In another display mode, such as with an ESI unit, the screen goes blank during computation time and then the last strobed image will be shown enhanced. With real time display, the system will blank the screen during computation and then the last stored image will be shown enhanced.

After automatic selection of one of the frames to be displayed, the system actually enhances all six images before placing the selected enhanced frame on the monitor 24. The operator can then select any one of the six stored and enhanced frames to be viewed on the monitor 24 in any order as determined from selection switches on the front panel. A cycle switch (not shown) causes the six stored enhanced images to cycle on the screen of the mointor 24 once per second, through techniques well known in the art. This is approximately real time when the six images are selected to represent a cardiac cycle.

Referring now to FIG. 5, a sequence of operations for converting data from an ultrasonascope to 30° sector display will be described. The system is also capable of resolution of wider angle sector displays.

As previously mentioned, sector data, while requiring only three or four bits for digitizing into a digital display alone, are digitized to eight bits resolution by converter 28 for image enhancement purposes.

The VPU 50 improves the data displayed in the following ways.

Data are originally obtained in polar coordinates. The VPU 50 converts these data to rectangular coordinates, through techniques well known in the art, for output to the system recorder and also interpolates the data to eliminate the distracting influences of the scan line and the blank areas between those scan lines.

For real time data and for the strobe mode, data routed through the system for display on the monitor is refreshed in the following manner:

For a 30° probe, the system saves 60–70 lines per frame (spaced at unequal angular intervals), interpolates 91 lines spaced equally every 166 degree based upon the stored data and displays the linearized 91 lines every 60th second. Every other field will be rotated 1/6 degree so that the two copies of the field present an interlaced, flicker-free image.

For wide angle probes, such as a probe approximating 81°, the system will store 108 lines per frame and display those lines 60 times/second. Similarly, every other field of 108 lines will be rotated ½ a line increment to present a flicker-free image of 216 lines.

The input data and the processed data both contain more dynamic range than can be displayed on either the monitor 24 or the strip chart recorder 81 of FIG. 5. A brightness transfer characteristic (BTC) curve, which is well known in the art, can be used to map 8-bit resolution data to 4-bit resolution data for display. Gamma correction is an important subclass and can be represented as a family of BTC curves. The gamma correction curves could be stored in a PROM for enabling the mapping of the data for display purposes.

The memory 48 is sufficient to store six 30° frames of 70 lines×256 elements/line×8 bits/element, or six wide-angle frames of 108 lines×256 element/line×8 bits/element, or one 120° frame. A portion of storage 48 is also used for storage of samples of the physiological parameters. In one embodiment, total storage capability is 1024 lines×256 element/line33 8 bits/element.

The control of the system and processing of the video information is performed by the VPU 50, which includes the AMD 2900 series devices previously described. The algorithms implemented with the system involve a large number of fixed point multiplications so that the 16×16 bit hardware multiplier 53 is incorporated. Programming is accomplished entirely by microcode incorporating 64 bit microcontrol words. The instruction speeds of the present implementation are as follows:

A. Basic microcycle—200 ns
B. Access to MOS main memory changing row or column only—600 ns
C. Access to MOS main memory changing both row and column—800 ns
D. Square of 16-bit number—600 ns
E. Multiplication of two 16-bit numbers (including loading of both operands and shifting result any number of bits to the right—800 ns
F. ALU instructions—200 ns
G. Most other instructions —400 ns The output controller 70 is capable of reading out data from the scan line buffers to the monitor 24. Prior to output of a frame of data, the VPU 50 can use a selected brightness transfer characteristic curve (BTC) previously described to convert 8 bit data to 4 bits. It then packs two adjacent lines into one line by placing the first line into the most significant 4 bits and the second line into the least significant 4 bits. The hardware of the output controller will then accept 8 bit data at the rate of which it could be read from main memory and split it into two output buffers. It then reads out first one buffer, then the next into a D/A converter such as converter 80 which will apply Z-modulation to monitor 24. The reason for packing and unpacking is to match the data rate needed by the CRT 24 with the slower information transfer rate of the MOS main memory 48. In CRT output modes, the hardware of the scan line buffers are reorganized into four scan line buffers of 512×4 bits of which only 256 picture elements of each line buffer are used.

The microprogram depicted in Appendix I is organized into three main sections which are data acquisition, computation and scan conversion.

The data acquisition portion of the program includes control of the digitizing of the input data, selection of the particular sectors to be displayed and storing of the raw digitized data in memory 48. During the data acquisition, the desired input sector data on bus 60, such as from a 30° probe, is digitized by input controller 23 in accordance with the frame select signals on bus 25 from front panel interface 40. The particular sectors to be displayed are selected in accordance with the frame select positions of FIG. 3. The input data on buses 60-64 are multiplexed in multiplexer 27 and digitized in converter 28 under control of control logic 30, and the digitized data are stored in main memory 48.

The next processor cycle is the computation portion. During the computation portion, the processor 50 performs the necessary computations upon the digitized data in memory 48 for the particular probe utilized. For example, in a 30° probe, the computation portion inludes a weighted averaging of the raw data scan lines in order to produce new scan lines spaced evenly 0.339° apart from +15.27° to −15.27° (91 ines). This is for the reason that, when using a 30° probe, it is desirable to convert from the natural angular increments (which are irregular) to a linearized set of angular increments. The weighted averages are generated by interpolation between the nearest pair of scan lines from the data stored in memory 48. For all sector sizes, image enhancement is performed on data in the polar coordinate system.

The lateral resolution of the stored data is improved by the following procedure:

Considering the data to be stored in rows corresponding to echoes from a single direction and presuming that adjacent rows correspond to data from different directions with a fixed angular increment from row to row, then select each column of data which represents all data from a single depth into the tissue.

Next, perform deconvolution on the column of data by removing the effects of the beam profile for that depth of tissue (e.g., perform a fast Fourier transform, multiply by a stored inverse in the frequency domain, and perform the inverse transform).

The next step is to write the deconvolved column of data over the original data in main memory.

Continue this procedure until all columns of the sector are so processed.

the scan conversion portion includes reading data stored in the polar coordinate system, computing horizontal lines to be displayed one at a time and loading them into the scan line buffers 71, 72 contained within output controller 70. The controller 70 then accomplishes transfer of the data to recorder 81. Output of the physiological data and patient identification also occurs at this time.

During the scan conversion portion, the enhanced data is converted by the processor 50 between polar coordinates and rectangular coordinates in accordance with well known techniques, utilizing the constants stored in PROM Tables 54, 55. The constants are depicted in Table A and Table B for the respective PROMs 54, 55 of FIG. 5.

The processor eliminates in the hard copy output the spaces between the original number of picture elements stored through interpolation between stored elements. (This process is naturally combined with the necessary scan conversion).

For a CRT display, the processor minimizes the spaces between the original scan lines by refreshing each original or enhanced line more than once and faster than real time, and each time moving it in angle to fill the gaps between the original lines. This is achieved by the processor enhancing the sector data to form an enhanced sector field for each image and interleaving corresponding enhanced scan lines at least twice. As a result, the spaces between the scan lines are reduced.

The output controller 70, under control of processor 50, transfers the enhanced and converted data from the scan line buffers 71, 72 out to the D/A converter 80 and recorder 81 (assuming the enhanced and converted data is to be recorded in hard copy form). The paper feed of recorder 81 is enabled via bus 82 and the physiological and other data such as a patient's I.D. number and time of day, together with the enhanced sector data from buffer 71, 72, is displayed on strip chart paper in a format such as depicted in FIG. 4. Once the selected sector data has been output by procesor 50, the recorder 81 is disabled and the system returns to the data acquisition cycle.

TABLE A

| 7718 | 7469 | 7281 | 7084 | 6890 | 6721 | 6553 | 6393 | 6241 | 6096 |
|------|------|------|------|------|------|------|------|------|------|
| 5957 | 5825 | 5693 | 5577 | 5461 | 5349 | 5242 | 5140 | 5041 | 4946 |
| 4854 | 4766 | 4681 | 4599 | 4519 | 4443 | 4369 | 4297 | 4228 | 4161 |
| 4096 | 4032 | 3971 | 3912 | 3855 | 3799 | 3744 | 3692 | 3640 | 3591 |
| 3542 | 3495 | 3440 | 3404 | 3360 | 3318 | 3276 | 3236 | 3196 | 3150 |
| 3120 | 3084 | 3048 | 3013 | 2978 | 2945 | 2912 | 2860 | 2849 | 2818 |
| 2783 | 2759 | 2730 | 2702 | 2674 | 2617 | 2621 | 2595 | 2570 | 2545 |
| 2520 | 2496 | 2473 | 2449 | 2427 | 2404 | 2383 | 2361 | 2340 | 2319 |
| 2299 | 2279 | 2250 | 2240 | 2221 | 2202 | 2184 | 2166 | 2149 | 2131 |
| 2114 | 2097 | 2080 | 2064 | 2048 | 2032 | 2016 | 2001 | 1905 | 1971 |
| 1956 | 1941 | 1927 | 1913 | 1899 | 1805 | 1872 | 1859 | 1846 | 1833 |
| 1820 | 1807 | 1795 | 1703 | 1771 | 1759 | 1747 | 1736 | 1724 | 1713 |
| 1702 | 1691 | 1680 | 1669 | 1659 | 1648 | 1638 | 1628 | 1618 | 1608 |
| 1598 | 1588 | 1579 | 1569 | 1560 | 1551 | 1542 | 1533 | 1524 | 1515 |
| 1506 | 1497 | 1489 | 1481 | 1472 | 1464 | 1456 | 1448 | 1440 | 1432 |
| 1424 | 1416 | 1409 | 1401 | 1394 | 1387 | 1379 | 1372 | 1365 | 1358 |
| 1351 | 1344 | 1337 | 1330 | 1323 | 1317 | 1310 | 1304 | 1297 | 1291 |
| 1285 | 1278 | 1272 | 1266 | 1260 | 1254 | 1248 | 1242 | 1236 | 1230 |
| 1224 | 1219 | 1213 | 1208 | 1202 | 1197 | 1191 | 1186 | 1180 | 1175 |
| 1170 | 1165 | 1159 | 1154 | 1149 | 1144 | 1139 | 1134 | 1129 | 1125 |
| 1120 | 1115 | 1110 | 1106 | 1101 | 1096 | 1092 | 1087 | 1083 | 1078 |
| 1074 | 1069 | 1065 | 1061 | 1057 | 1052 | 1048 | 1044 | 1040 | 1036 |
| 1032 | 1028 | 1024 | 1020 | 1016 | 1012 | 1008 | 1004 | 1000 | 996  |
| 992  | 989  | 985  | 981  | 978  | 974  | 970  | 967  | 963  | 960  |
| 956  | 953  | 949  | 946  | 942  | 939  | 936  | 932  | 929  | 926  |
| 923  | 919  | 916  | 913  | 910  | 907  | 903  | 900  | 897  | 894  |
| 891  | 888  | 885  | 882  | 879  | 876  | 873  | 870  | 868  | 865  |
| 862  | 859  | 856  | 853  | 851  | 848  | 845  | 842  | 840  | 837  |
| 834  | 832  | 829  | 826  | 824  | 821  | 819  | 816  | 814  | 811  |
| 809  | 806  | 804  | 801  | 799  | 796  | 794  | 791  | 789  | 787  |
| 784  | 782  | 780  | 777  | 775  | 773  | 771  | 768  | 766  | 764  |
| 762  | 759  | 757  | 755  | 753  | 751  | 748  | 746  | 744  | 742  |
| 740  | 738  | 736  | 734  | 732  | 730  | 728  | 726  | 724  | 722  |
| 720  | 718  | 716  | 714  | 712  | 710  | 708  | 706  | 704  | 702  |
| 700  | 699  | 697  | 695  | 693  | 691  | 689  | 688  | 686  | 684  |
| 682  | 680  | 679  | 677  | 675  | 673  | 672  | 670  | 668  | 667  |
| 665  | 663  | 661  | 660  | 658  | 657  | 655  | 653  | 652  | 650  |
| 648  | 647  | 645  | 644  | 642  | 640  | 639  | 637  | 636  | 634  |
| 633  | 631  | 630  | 628  | 627  | 625  | 624  | 622  | 621  | 619  |
| 618  | 616  | 615  | 613  | 612  | 611  | 609  | 608  | 606  | 605  |
| 604  | 602  | 601  | 599  | 598  | 597  | 595  | 594  | 593  | 591  |
| 590  | 589  | 587  | 586  | 585  | 583  | 582  | 581  | 579  | 578  |
| 577  | 576  | 574  | 573  | 572  | 571  | 569  | 568  | 567  | 566  |
| 564  | 563  | 562  | 561  | 560  | 558  | 557  | 556  | 555  | 554  |
| 553  | 551  | 550  | 549  | 548  | 547  | 546  | 544  | 543  | 542  |
| 541  | 540  | 539  | 538  | 537  | 536  | 534  | 533  | 532  | 531  |
| 530  | 529  | 528  | 527  | 526  | 525  | 524  | 523  | 522  | 521  |
| 520  | 519  | 518  | 517  | 516  | 515  | 514  | 513  | 512  | 511  |
| 510  | 509  | 508  |      |      |      |      |      |      |      |

TABLE B

| 194   | 582   | 970   | 1358  | 1746  | 2135  | 2524  | 2912  | 3301  | 3691  |
|-------|-------|-------|-------|-------|-------|-------|-------|-------|-------|
| 4080  | 4470  | 4860  | 5230  | 5641  | 6032  | 6424  | 6816  | 7209  | 7602  |
| 7995  | 8390  | 8784  | 9180  | 9576  | 9973  | 10370 | 10768 | 11167 | 11567 |
| 11968 | 12369 | 12772 | 13175 | 13579 | 13995 | 14391 | 14798 | 15207 | 15616 |
| 16027 | 16439 | 16852 | 17267 | 17682 | 18993 | 32220 |       |       |       |

The constants contained within Table A are depicted according to the inverse of the value of x, for the reason that it is faster to manipulate the necessary data using multiplication rather than division, thus decreasing processing time required to compute y/x. Table B contains the arctan values of y/x.

In summary, then, the present invention provides the following features:

(1) A hard copy of multiple sector scans which can be stored in rapid sequence to capture motion of moving a structure such as the heart. This can be displayed on the same strip chart that is utilized for M-mode purposes.

(2) Elimination of the need for an instant camera for recording a sector image.

(3) Providing capability of capturing a patient's cardiac profile in the same cycle.

(4) Writing of patient's identification number and time of day together with the digitized data and physiological parameters.

(5) A high-resolution hard copy of a single sector scan to be used for slowly moving structures such as the abdominal organs.

(6) A soft copy of a sector scan on a cathode ray tube, (7) Using digital techniques for image enhancement, particularly with regard to improving the lateral resolution through deconvolution techniques.

(8) Elimination of noticeable scan lines.

APPENDIX I

TO SPECHT ET AL APPLICATION NO.

filed

```
WORD 64
; I/O COMMANDS
CMD0:   EQU H#0
CMD1:   EQU H#1
CMD2:   EQU H#2
CMD3:   EQU H#3
CMD4:   EQU H#4
CMD5:   EQU H#5
CMD6:   EQU H#6
CMD7:   EQU H#7
CMD8:   EQU H#8
CMD9:   EQU H#9
CMD10:  EQU H#A
CMD11:  EQU H#B
CMD12:  EQU H#C
CMD13:  EQU H#D
CMD14:  EQU H#E
CMD15:  EQU H#F
; B ADDRESS
B0:     EQU H#0
B1:     EQU H#1
B2:     EQU H#2
B3:     EQU H#3
B4:     EQU H#4
B5:     EQU H#5
B6:     EQU H#6
B7:     EQU H#7
B8:     EQU H#8
B9:     EQU H#9
B10:    EQU H#A
B11:    EQU H#B
B12:    EQU H#C
B13:    EQU H#D
B14:    EQU H#E
B15:    EQU H#F
; EXTERNAL FILE IF FILEN, OTHERWISE R0-R15 GIVES A ADDRESS
R0:     EQU B#00000
R1:     EQU B#00001
R2:     EQU B#00010
R3:     EQU B#00011
R4:     EQU B#00100
R5:     EQU B#00101
R6:     EQU B#00110
R7:     EQU B#00111
R8:     EQU B#01000
R9:     EQU B#01001
R10:    EQU B#01010
R11:    EQU B#01011
R12:    EQU B#01100
R13:    EQU B#01101
R14:    EQU B#01110
R15:    EQU B#01111
R16:    EQU B#10000
R17:    EQU B#10001
R18:    EQU B#10010
R19:    EQU B#10011
R20:    EQU B#10100
R21:    EQU B#10101
R22:    EQU B#10110
```

```
        R23:  EQU  B#10111
        R24:  EQU  B#11000
        R25:  EQU  B#11001
        R26:  EQU  B#11010
        R27:  EQU  B#11011
        R28:  EQU  B#11100
        R29:  EQU  B#11101
        R30:  EQU  B#11110
        R31:  EQU  B#11111
        ;ALU DESTINATION
        QREG:  EQU  Q#0
        NOP:   EQU  Q#1
        RAMA:  EQU  Q#2
        RAMF:  EQU  Q#3
        RAMQD: EQU  Q#4
        RAMD:  EQU  Q#5
        RAMQU: EQU  Q#6
        RAMU:  EQU  Q#7
        ;ALU FUNCTION
        ADD:   EQU  Q#0
        SUBR:  EQU  Q#1
        SUBS:  EQU  Q#2
        OR:    EQU  Q#3
        AND:   EQU  Q#4
        NOTRS: EQU  Q#5
        EXOR:  EQU  Q#6
        EXNOR: EQU  Q#7
        ;ALU SOURCE
        AQ:  EQU  Q#0
        AB:  EQU  Q#1
        ZQ:  EQU  Q#2
        ZB:  EQU  Q#3
        ZA:  EQU  Q#4
        DA:  EQU  Q#5
        DQ:  EQU  Q#6
        DZ:  EQU  Q#7
        ;MICRO CONTROL
        CJPL:  EQU  H#3    ;CJP
        CRET:  EQU  H#A    ;CRTN
        LDCTR: EQU  H#C    ;LDCT
        ;STATUS MASK
        FZNP:   EQU  H#10
        FZPN:   EQU  H#20
        DONE:   EQU  H#40
        FMIN:   EQU  H#80
        FMAX:   EQU  H#100
        DGTIZE: EQU  H#200
        ;
        ;ALU: DESTINATION, FUNCTION, SOURCE, DEFAULT CIN=0, CONTINUE
        ALU: DEF 3V, 3V, 3V, 26X, 1VB#0, 12X, 4VH#E, 12V%X
        ;
        ;SET REGISTERS: A/R REG, DEFAULT R/W=1, B REG
        REG: DEF 9X, 5VX, 1VB#1, 4VX, 45X ;DEFAULT EXTERNAL FILE READ
        ;
        ;INPUT COMMANDS
        IMMED: DEF 19X, Q#1, 42X
        PROME: DEF 19X, Q#2, 42X
        ZEN:   DEF 19X, Q#3, 42X
        SFTEN: DEF 19X, Q#4, 42X
        FILEN: DEF 19X, Q#5, 42X
        ;
        ;DESTINATION COMMANDS
        LDADR: DEF 22X, 5Q#20:, 37X
        LDAY:  DEF 22X, 5Q#22:, 37X
        LDD:   DEF 22X, 5Q#10:, 37X
        LDX:   DEF 22X, 5Q#4%, 37X
        LDY:   DEF 22X, 5Q#2%, 37X
        LDXY:  DEF 22X, 5Q#6%, 37X
        RTOX:  DEF 22X, 5Q#5%, 37X
        ;
```

```
; I/O CONTROL DEVICE NO.
BULKM:  DEF 27X, H#0, 4V, 1X, 7H#8%, 21X  ; BUSRQ
ICTRL:  DEF 27X, H#1, 4V, 1X, 7H#8%, 21X
OCTRL:  DEF 27X, H#2, 4V, 1X, 7H#8%, 21X
FRONTP: DEF 27X, H#4, 4V, 1X, 7H#8%, 21X
SHIFT:  DEF 27X, H#F, 4VH#0, 29X      ; DEFAULT CMD0 (NO SHIFT)
;
; CONTROL
CIN:   DEF 35X, B#1, 28X
LDZ:   DEF 36X, 7H#1%, 21X
DEN:   DEF 36X, 7H#A%, 21X
ZDBUS: DEF 36X, 7H#B%, 21X
VPUDN: DEF 36X, 7H#4%, 21X
BUSRQ: DEF 36X, 7H#8%, 21X
LDML:  DEF 36X, 7H#10:, 21X
INDIR: DEF 36X, 7H#2B:, 21X
HOLD:  DEF 36X, 7H#40:, 21X
;
; TEST CONDITIONS (DEFAULT T/F=1)
CNTR:  DEF 43X, H#0, 1VB#1, 16X
SIGN:  DEF 43X, H#1, 1VB#1, 16X
ZERO:  DEF 43X, H#2, 1VB#1, 16X
CARRY: DEF 43X, H#3, 1VB#1, 16X
OVFL:  DEF 43X, H#4, 1VB#1, 16X
RAM0:  DEF 43X, H#5, 1VB#1, 16X
RSYNC: DEF 43X, H#6, 1VB#1, 16X
TSYNC: DEF 43X, H#7, 1VB#1, 16X
RWAVE: DEF 43X, H#8, 1VB#1, 16X
FIFO:  DEF 43X, H#9, 1VB#1, 16X
SCAN:  DEF 43X, H#A, 1VB#1, 16X
VPU1:  DEF 43X, H#B, 1VB#1, 16X
VPU2:  DEF 43X, H#C, 1VB#1, 16X
VPU3:  DEF 43X, H#D, 1VB#1, 16X
FSWTCH: DEF 43X, H#E, 1VB#1, 16X
GND:   DEF 43X, H#F, 1VB#0, 16X
;
; MICRO CONTROL
JZ:    DEF 48X, H#0, 12V%X
CJS:   DEF 48X, H#1, 12V%X
JMAP:  DEF 48X, H#2, 12V%X
CJP:   DEF 48X, H#3, 12V%X
PUSH:  DEF 48X, H#4, 12V%X
JSRP:  DEF 48X, H#5, 12V%X
CJV:   DEF 48X, H#6, 12V%X
JRP:   DEF 48X, H#7, 12V%X
RFCT:  DEF 48X, H#8, 12V%X
RPCT:  DEF 48X, H#9, 12V%X
CRTN:  DEF 48X, H#A, 12V%X
CJPP:  DEF 48X, H#B, 12V%X
LDCT:  DEF 48X, H#C, 12V%X
LOOP:  DEF 48X, H#D, 12V%X
CONT:  DEF 48X, H#E, 12V%X
JP:    DEF 48X, H#F, 12V%X
SKIP:  DEF 48X, H#3, 12V#D#2   ; DEFAULT JMP PC+2
;
; SPECIAL COMMANDS
INR:   DEF 0#303, 6X, 4V, 16X, B#1, 12X, 4VH#E, 12V%X  ; INR B ADR, AND CONT
DCR:   DEF 0#303, 6X, 4V, 16X, B#0, 12X, 4VH#E, 12V%X  ; DCR B ADR, AND CONT
MOV:   DEF 0#334, 5V%, B#1, 4V, 3VX, 26X, 4VH#E, 12V%X ; MOV REG A TO REG B
NEG:   DEF 0#303, 6X, 4V, 16X, B#1, 12X, 4VH#E, 12V%X  ; NEG REG B
LDI:   DEF 0#337, 6X, 4V, 0#1, 26X, H#E, 12V%X   ; LOAD IMMED, B ADR
TEST:  DEF 0#145, 5H#F%, 5X, 0#1, 26X, H#E, 12V%  ; TEST STATUS A 15 & CONT
SETS:  DEF 0#335, 5H#F%, 1X, H#F, 29X, H#E, 12V%  ; SET STATUS B 15 & CONT
CALL:  DEF 43X, H#F, B#0, H#1, 12V%X  ; UNCONDITIONAL CALL
END
ORG 0
PHYSS:  EQU 0
PHYSE:  EQU 0
NLARGE: EQU 0
```

```
        ERROR:  EQU 0
        DIV:    EQU 0
        SETF:   EQU 0
        BEGIN:  FRONTP CMD12 & CONT              ;REPEAT PICTURE ?
                ALU NOP,OR,DZ,,CJPL,PROCES & LDZ & ZEN & ZERO 0   ;JMP IF YES
                FRONTP CMD13 & CONT              ;ENLARGE SECTOR ?
                ALU NOP,OR,DZ,,CJPL,NLARGE & LDZ & ZEN & ZERO 0   ;JMP IF YES
                RSYNC 0 & CJP BEGIN              ;LOOP UNTIL RSYNC
        ;FIND MIN, MAX, AND ZERO POINT FOR INITIAL SET-UP
        MMZ:    LDI B2,0
                LDI B7,0
                LDI B11,0
                ALU NOP,OR,DZ,,PHYSS
                ALU RAMF,OR,DZ & REG ,,B6 & PROME    ;(PHYSS) TO B6
        WAIT:   RWAVE 0 & CJP WAIT               ;WAIT FOR RWAVE
                FRONTP CMD1 & ALU RAMF,AND,ZB & REG ,,B15    ;RESET RWAVE
                FRONTP CMD7 & ALU NOP,ADD,ZA,,,H#FFE & REG R1,0
                LDZ & ZEN & ALU RAMF,OR,DA & REG R15,,B15
        STAR:   CALL DATAR
        SLOPE:  CALL PROBE
                ALU NOP,SUBS,AB & REG R0,,B1            ;A0-B1
                CJP SLOPE & CARRY 0
        MINMAX: CALL PROBE
                ALU NOP,SUBS,AB & REG R0,,B1
                CJP MINMAX & CARRY               ;JMP IF B1>A0
                ALU NOP,OR,ZB & REG R5,0,B0              ;B0 TO MAX
        MAXMIN: CALL PROBE
                ALU NOP,SUBS,AB & REG R0,,B1
                CJP MAXMIN & CARRY 0             ;JMP IF B1<A0
                ALU QREG,OR,ZB & REG R4,0,B0     ;B0 TO MIN,Q
                ALU QREG,ADD,DQ & FILEN & REG R5    ;MIN+MAX TO Q
                ALU RAMD,OR,ZQ & REG ,,B8 & SHIFT   ;Q/2 TO ZERO
                INR B11
                RWAVE 0 & CJP STAR               ;JMP IF NOT RWAVE
        CHECK:  FRONTP CMD1 & ALU NOP,SUBR,DA,,,D#15 & REG R11 & IMMED
                CJP ERROR & CARRY 0
                ALU NOP,SUBR,DA,,,D#60 & REG R11 & IMMED    ;A11-60
                CJP ERROR & CARRY & FRONTP CMD3             ;JMP IF A11>60, RST
        ;READ FRONT PANEL, CALCULATE SECTORS TO STORE
                LDI B3,0
                LDI B4,1
        MORE:   ICTRL CMD6 & ALU NOP,OR,ZB & LDADR
                LDZ & ZEN & ALU NOP,OR,DZ & LDX
                ALU NOP,OR,ZB & REG ,,B11 & LDY          ;R11 TO Y
                LDML & ALU RAMF,OR,DZ,,,H#FF & REG R12,0,B12 & IMMED
                SHIFT CMD0 & SFTEN & ALU RAMF,OR,DZ & REG ,,B14    ;LSB TO B14
                SHIFT CMD15 & SFTEN & ALU RAMD,OR,DZ & REG ,,B13   ;MSB TO B13
                CALL DIV                 ;CALL DIVIDE
                ALU NOP,OR,ZQ            ;REMAINDER ?
                SKIP & ZERO              ;JMP PC+2 IF NO
                INR B14                  ;INR QUOTIENT
                ALU NOP,ADD,DA,0,,D#21 & REG R4 & INDIR
                ALU NOP,OR,ZB & REG ,0,B14
                ALU RAMF,OR,ZA & REG R14,,B3             ;MOVE QUOTIENT TO R3
                INR B4                   ;INR SECTOR COUNT
                ALU NOP,SUBR,DA,,,D#7 & REG R4 & IMMED
                CJP MORE & CARRY         ;JMP IF <7 (NO)
        START:  TEST FZNP                ;FND ZRO, N-P ?
                SKIP 3 & ZERO            ;YES, JMP PC+3
                CJP FSSET & FSWTCH       ;JMP IF FOOTSWITCH SET
                CJP CHECK & RWAVE        ;JMP IF RWAVE
                CJP THETA & RSYNC 0      ;JMP IF NOT RSYNC
                CALL PROBE
        ;FIND ZERO, START AND STOP DIGITIZE
                ALU RAMQU,AND,DA,,,H#10 & REG R15,,B3 & IMMED & SHIFT
                ZERO 0 & ALU RAMQU,AND,AQ,,CJPL,NFZNP & REG R15,,B3 & SHIFT
                ZERO 0 & ALU NOP,AND,AQ,,CJPL,NFZPN & REG R15
                CJP CNTRZ & ZERO
                ALU NOP,SUBS,DZ & REG R0,0        ;DCR 35 LINE CNTR
                CJP CNTNZ & ZERO 0                ;JMP IF CNTR NOT ZERO
```

```
                ICTRL CMD11 & SETS DONE
                ALU NOP,ADD,DA,,,D#29 & INDIR & REG R10 & IMMED
                ALU NOP,OR,ZB & REG ,0,B6          ;STORE LLVD INDIRECT
                INR B11                  ;INR RFC
                INR B10                  ;INR DFC
CNTRZ:  TEST FMIN                ;FOUND MIN ?
                CJP FNDMIN & ZERO 0      ;JMP IF YES
CNTNZ:  ALU NOP,SUBS,AB & REG R0,,B1      ;A0-B1
                CARRY 0 & ALU QREG,OR,ZA,,CJPL,NFMIN & REG R0
                ALU NOP,OR,ZB & REG R4,0,B0       ;B0 TO MIN
                SETS FMIN
                ALU RAMD,ADD,D0 & REG R5,,B8 & FILEN & SHIFT
FZRO:   TEST DGTIZE              ;DIGITIZE ?
                ZERO & ALU RAMF,AND,ZB,,CJPL,START & REG ,,B4    ;JMP IF NO
                ALU NOP,OR,ZA,,LDCTR,D#256 & REG R6 & LDADR & BULKM CMD9
EMPTY:  FIFO & BUSRQ & CJP EMPTY
                ALU NOP,OR,ZA & REG R4 & LDADR & BULKM CMD14
                ALU RAMF,ADD,ZB,,RPCT,EMPTY & REG ,,B4 & BUSRQ
;FOUND MIN, RESET ALL STATUSES
FNDMIN: ALU RAMF,AND,DA,,,D#7 & REG R15,,B15 & IMMED
                JP FZRO
;NOT FOUND ZERO, NEG-POS, KEEP LOOKING
NFZNP:  ALU NOP,SUBS,AB & REG R8,,B1     ;ZER0-B1
                CJP FZRO & CARRY 0       ;JMP IF ZERO>B1
                SETS FZNP                ;FOUND ZERO
                DCR B5                   ;DCR FSC
                CJP SETF & ZERO 0        ;JMP IF NOT ZERO
                SETS DGTIZE              ;SET STATUS, DIGITIZE
                ALU NOP,OR,ZA & REG R10
                PROME & ALU RAMF,OR,DZ & REG ,,B9         ;BMSA
                ALU RAMF,ADD,DA,0,,D#30 & REG R9,,B9 & IMMED    ;BMSSA
                INR B10                  ;INR DFC
                ALU NOP,ADD,DA,0,,D#21 & REG R10 & INDIR & IMMED
                ALU RAMF,OR,DZ & REG ,,B5 & FILEN
                ICTRL CMD12 & CJP FZRO & GND
;NOT FOUND MAX, KEEP LOOKING
NFMAX:  ALU RAMF,OR,ZA,,CJPL,CONTL & REG R1,,B0 & GND
;NOT FOUND ZERO, POS-NEG
NFZPN:  TEST FMAX                ;FOUND MAX ?
                ZERO 0 & ALU NOP,SUBS,AB,,CJPL,CONTL & REG R0,B1
                CJP NFMAX & CARRY        ;JMP IF B1>A0
                ALU NOP,OR,ZB & REG R5,0,B0       ;B0 TO MAX
                SETS FMAX
CONTL:  ALU NOP,SUBR,AB & REG R8,,B1     ;B1-A8
                CJP FZRO & CARRY 0
                ALU NOP,OR,DZ,,,D#35 & REG R0,0 & IMMED    ;35 TO R0
                SETS FZPN
NFMIN:  ALU RAMF,OR,ZA,,CJPL,FZRO & REG R1,,B0 & GND
;CHECK IF THETA SYNC HAS OCCURRED, AND IF IT HAS, WAIT 4 R-SYNCS
;ALSO INR THE BULK MEMORY ROW ADDRESS BY 5
THETA:  CJP START & TSYNC 0      ;JMP IF TSYNC=0
                TEST DGTIZE & FRONTP CMD2
                CJP DZNTD & ZERO 0
                ALU NOP,ADD,DA,,,D#35 & REG R10 & IMMED & INDIR
                ALU NOP,OR,ZB & REG ,0,B9
DZNTD:  ALU RAMF,OR,DZ,,LDCTR,D#4 & REG ,,B4
GOON:   CALL DATAR
                RPCT GOON
                JP START
;SUBROUTINE TO PERFORM A 20USEC WAIT LOOP
TIME:   LDI R4,D#32
                DCR R4
                CJP TIME & ZERO 0
                CRTN & GND
;SUBROUTINE TO READ AND STORE THE PROBE POSITION AND
;PHYSIOLOGICAL DATA
PROBE:  ALU RAMF,OR,ZA & REG R1,,B0
DATAR:  CJP DATAR & RSYNC 0      ;LOOP UNTIL RSYNC
DATA:   CALL TIME
```

```
                ICTRL CMD10 & CONT
                ZEN & LDZ & ALU RAMF,OR,DZ & REG ,,B1
                CALL TIME
    PHYSD:      ALU NOP,SUBS,DZ & REG R1,0, & FILEN
                ZERO 0 & ALU QREG,AND,DA,,CRET,H#1 & REG R15
                ZERO & ALU NOP,ADD,ZQ,1,CJPL,RECORD & REG R1,0
                ALU RAMD,OR,ZA & REG R2,,B3 & SHIFT
                DCR B3,H#3,PHONO & ZERO
                DCR B3,H#3,PRESR & ZERO
                ICTRL CMD3 & CONT          ;GET PULSE
    CONTU:      LDZ & INR R2
                ALU RAMQU,AND,DA & REG R15,,B3 & SHIFT
                ZERO 0 & ALU QREG,AND,AQ,,CJPL,NOMRK & REG R8
                ALU NOP,OR,ZQ & ZDBUS & LDD
    NOMRK:      ALU NOP,OR,ZA & REG R6 & LDADR
                BULKM CMD9 & ALU NOP,OR,ZA & REG R7 & LDADR
                BULKM CMD10 & ALU NOP,OR,DZ & ZEN & LDD
                DEN & INR B7
                ALU QREG,AND,DA,,CRET,H#100 & REG R7 & ZERO
                LDI B7,0
                INR B6
                ALU NOP,OR,DZ,,,PHYSE & IMMED
                ALU NOP,SUBR,DA & PROME & REG R6
                CRTN & CARRY
                ALU NOP,OR,DZ,,,PHYSS & IMMED
                ALU RAMF,OR,DZ,,CRTN & REG ,,B6 & PROME & GND
    PRESR:      ICTRL CMD1 & CJP CONTU & GND       ;GET PRESSURE
    PHONO:      ICTRL CMD0 & CJP CONTU & GND       ;GET PHONO
    RECORD:     ALU NOP,OR,DZ,,,D#11 & REG R1,0
    EKG:        ICTRL CMD2 & CJP CONTU & GND       ;GET EKG
    ;FOOTSWITCH PRESSED, READ NO. OF FRAMES IN 1 RWAVE THEN PROCESS
    FSSET:      FRONTP CMD0 & MOV R3,B3,0#5
    BACK:       RSYNC 0 & CJP BACK
                CALL TIME
                CALL TIME
                CALL PHYSD
                DCR B3
                CJP BACK & ZERO 0
    END
    MIDPT EQU 0
    ORG H#100
    ;ROUTINE TO PERFORM WEIGHTED AVERAGING BY TAKING THE TWO
    ;CLOSEST INPUT LINES TO AN ARTIFICIAL OUTPUT LINE AND TAKE
    ;THE WEIGHTED AVERAGE OF THAT LINE.
    AVG:LDI B0,D#6
    INIT:ALU NOP,ADD,DA,,,D#13 & REG R0 & INDIR & IMMED
        ALU RAMA,OR,DZ & REG R0,,B5 & FILEN
        ALU NOP,OR,DZ & REG R0,0 & PROME
        ALU NOP,ADD,DA,,,D#35 & REG R0 & IMMED & INDIR
        ALU RAMF,OR,DZ & FILEN & REG ,,B9
        CJP OVERH & ZERO 0
        ALU NOP,ADD,DA,,,D#41 & REG R0 & INDIR & IMMED
        ALU RAMF,OR,DZ & REG ,,B15 & FILEN
    OVERH:LDI B4,D#91
    D211:MOV R8,B2
        MOV R15,B3
        ALU NOP,OR,DZ & REG R0 & FILEN & LDX
        ALU NOP,OR,DZ,,,D#679 & IMMED & LDY
        LDI B12,D#32000 & LDML
        ALU RAMF,OR,DZ,,LDCTR,D#71 & REG ,,B1 & SHIFT CMD1 & SFTEN
        ALU RAMF,OR,ZA & REG R4,0,B5
    CHECK:ALU RAMF,OR,ZA & REG R2,,B2
        ALU NOP,SUBS,AB,,CJPL HEADX & REG R2,,B5 & ZERO
        CJP ZEROX & ZERO
        ALU NOP,ADD,DA,,MIDPT & REG R5 & IMMED
        ALU RAMF,SUBS,DA & REG R1,,B11 & PROME
        ALU NOP,SUBR,AB,,CJPL,BCK & REG R11,,B12 & SIGN
        CJP BCK & SIGN
        ALU NOP,OR,ZB & REG R5,0,B5
```

```
          MOV R11,B12
BCK:      INR B5,H#9,CHECK
CKER:     ALU RAMF,ADD,DZ & REG R5,,B7 & FILEN
          MOV R8,B2
          ZERO & ALU NOP,SUBR,AB,,CJPL CROSX & REG R7,,B2
          CJP CRX & ZERO 0
          ALU RAMF,ADD,DA,,,D#5 & REG R7,,B7 & IMMED
CRX:      ALU NOP,ADD,DA,,,MIDPT & REG R7 & IMMED
          ALU RAMF,SUBR,DA & REG R1,,B9 & PROME
          CJP PLUS & SIGN 0
          NEG B9
PLUS:     ALU RAMF,ADD,AB & REG A9,,B12
          CJP PLUSR & SIGN & HOLD
          CJP PLUSR & ZERO
          ALU NOP,OR,DZ,,,D#128 & LDX & IMMED
          ALU NOP,OR,ZA & REG R9 & LDY
          LDML & CONT
          ALU RAMD,OR,DZ & REG ,,B13 & SFTEN & SHIFT CMD15
          ALU RAMF,OR,DZ & REG ,,B14 & SHIFT & SFTEN
          CALL DIV
          ALU RAMF,SUBS,DA,,,D#128 & REG R11,,B10 & IMMED
          ALU RAMF,AND,ZB,,,LDCTR D#256 & REG ,,B11
LOOPH:    ALU NOP,OR,ZA & REG R5 & BULKM CMD7 & LDADR
          ALU NOP,OR,DZ & REG R5 & FILEN & BULKM CMD8 & LDADR
          ALU NOP,OR,ZA & REG R11 & LDX & BUSRQ
          VPUDN & CONT
          ALU NOP,OR,DZ & LDZ & ZEN & LDY
          ALU NOP,OR,ZA & REG R7 & LDML & ICTRL CMD8 & LDADR
          ALU RAMF,OR,DZ & REG ,,B1 & SFTEN & BUSRQ
          ALU NOP,OR,AO & R10 & LDX
          ALU NOP,OR,DZ & LDZ & ZEN & LDX
          ALU NOP,OR,DZ,,,1 & LDML & LDY & IMMED
          ALU RAMF,ADD,DA & REG R1,,B1 & SFTEN & SHIFT & LDX
          ALU NOP,OR,ZA & REG R6 & LDML & LDADR & BULKM CMD8
          ALU RAMF,OR,DZ & REG ,,B1 & SHIFT CMD8 & SFTEN & BUSRQ
          ALU NOP,OR,ZA & REG R1 & LDD & DEN
          INR B5,H#9,LOOPH & CARRY
          DCR B4
          ALU NOP,ADD,DZ,1,CJPL,DOIT & REG R0,0 & FILEN & ZERO 0
          DCR B0
          CJP INIT & ZERO 0
;ROUTINE TO PERFORM IMAGE ENHANCEMENT
IMAGE:    LDI B0,D#6
NEXTF:    LDI B6,D#256
          ALU NOP,OR,ZA & REG R0
          ALU RAMF,OR,DZ & REG ,,B5 & PROME
NEXTR:    ALU NOP,OR,ZA & REG R6 & LDADR & BULKM CMD11
          BUSRQ & LDCT D#91
          CALL CALCU
NEXTN:    MOV R1,B3
          MOV R2,B4
          INR B5,H#9,NEXT
          CALL CALCU
          ALU NOP,SUBS,AB & REG R4,,B1
          ALU NOP,SUBR,AB,,CJPL,NEXTC & REG R3,,B2 & SIGN
          CJP NEXTN & SIGN 0
          ALU NOP,OR,ZA & REG R5 & LDADR & BULKM CMD8
          BUSRQ & CONT
          ALU NOP,AND,ZA,,JPL NEXTN & REG R0 & LDD & DEN & JP NEXTN
NEXTC:    ALU NOP,ADD,ZA,1 & REG R5 & LDADR & BULKM CMD8 & JP BCKH
NEXT:     DCR B6
          CJP NEXTR & ZERO 0
          DCR B0
          CJP NEXTF & ZERO 0
          JP OUTPT
;SUBROUTINE TO READ CONTENTS OF MEMORY AND CALCULATE 12.5% DIFFERENCE
CALCU:    ALU NOP,OR,ZA & LDADR & REG R7 & BULKM CMD8
          BUSRQ & CONT
          ALU NOP,OR,DZ,,,D#1 & LDY
          ALU RAMF,OR,DZ & REG ,,B1 & LDZ & ZEN & LDX
          LDML & CONT
```

```
         ALU RAMF,ADD,DA,,,CRET & REG R1,,B2 & SHIFT CMD3 & SFTEN & GND
         ;SUBROUTINE TO PERFORM DIVISION
         ;B12      DIVISOR
         ;B13,14 MSB,LSB DIVIDEND
         ;B13     QUOTIENT
         ;Q REG   REMAINDER
         DIV:ALU QREG,OR,ZA,,LDCTR D#17 & REG R13
         DIVL:ALU RAMQU,OR,ZB & REG ,,B14 & SHIFT CMD2
         ALU NOP,SUBR,AQ & REG R12
         CJP NZAD & CARRY
         ALU QREG,SUBR,AQ & REG R12
         ALU RAMF,AND,DA & REG ,,B14 & CONT H#FE & IMMED
         NZAD:ALU RAMF,OR,ZQ,,RPCTR,DIVL & REG ,,B11
         CRTN & GND
         ;
         HEADX:ALU NOP,OR,ZA & REG R3
         ALU RAMF,SUBR,ZB,,CJPL BCKH & REG ,,B3 & ZERO 0
         INR B5,H#9,BCK
         JP CKER
         ZEROX:LDI B2,0
         LDI B3,D#65
         ALU RAMF,ADD,DZ,,,D#4 & REG A5,,B5 & IMMED
         ALU QREG,OR,DZ,,,D#5
         ZEROR:   ALU QREG,SUBR,ZQ
         CJP BCK & ZERO
         RPCT ZEROR
         JP CKER
         CROSX:ALU RAMF,SUBR,ZA & REG R15,,B3
         CJP CRX & ZERO
         ALU RAMF,ADD,DZ,,,D#2 & REG R7,,B7
         JP CRX
         END
         ORG H#200
         ;ROUTINE TO WRITE TWO 30 DEGREE SECTORS OUT ON THE E21
         SCONV:LDI B11,D#271
         SCANMT:CJP SCANMT & SCAN 0
         CALL ZSCAN
         LDI B9,D#1023
         LDI B10,D#483
         ALU RAMF,SUBR,DA,,,D#136 & REG R11,0,B1 & IMMED
         ALU NOP,OR,ZB,,CJPL,GREAT & REG ,,B1 & LDXY & SIGN 0
         NEG B1 & LDXY
         GREAT:LDI B2,0 & LDML
         ALU RAMF,OR,DZ & REG ,,B12 & SHIFT CMD1 & SFTEN
         ALU NOP,OR,DZ & REG R8,0 & SHIFT CMD4 & SFTEN
         LDI B3,D#4136
         LDI B4,D#516
         NEWEL:ALU NOP,ADD,DA,,,INVM & REG R4 & IMMEDM
         RTOX & CONT
         ALU NOP,OR,ZA & REG R1 & LDY
         LDML & CONT
         ALU RAMF,OR,DZ & REG ,,B5 & SFTEN & SHIFT CMD2
         ALU NOP,ADD,DA,,,IATAN & REG R2 & IMMED
         ALU NOP,SUBR,DA & REG R5 & PROME
         INR B2,H#3,TRYA & SIGN
         ALU NOP,SUBS,DA,,,D#46 & REG R2 & IMMED
         ALU NOP,ADD DZ,,CJPL,OUTH & R11 & FILEN & SIGN
         ALU RAMF,SUBS,ZA,,CJPL,OVRME & REG R2,,B5 & SIGN
         MOV R2,B5
         OVRME:ALU NOP,OR,ZA & REG R4 & LDXY
         ALU NOP,SUBR,DA,,,D#128 & REG R4 & LDML & IMMED
         ALU RAMF,ADD,DA,,CJPL LTOTE & REG R12,,B6 & SFTEN & SHIFT CMD1
         ALU RAMF,OR,DZ & REG ,,B6 & SFTEN & SHIFT CMD4
         ALU NOP,SUBS,DA,,,D#16700 & REG R6 & IMMED
         ALU RLDB,ADD,DA,,CJP NEAR & REG R12,,B6 & SIGN
         ALU RAMF,SUBR,DA,,,D#8 & REG R3,,B3 & LDXY & IMMED
         LDML & CONT
         ALU NOP,SUBR,DA & REG R6 & SFTEN & SHIFT CMD10
         ALU RAMF,ADD,ZB,,CJPL,AGAIN & REG ,,B3 & LDXY & SIGN 0
         EXNORPU:DCR B3 & LDX
         ALU NOP,OR,DZ,,,D#271 & IMMED & LDY
```

```
ALU QREG,OR,DZ,,,D#144 & LDML4
ALU RAMF,SUBS,DQ & REG ,,B7 & SFTEN & SHIFT CMD9
CJP SKIP & SIGN 0
LDI B7,0
SKIP:ALU RAMF,AND,DZ,,,H#7 & REG R7,,B8
ALU NOP,SUBR,DA,,,H#4 & REG R4
ALU RAMQD,OR,ZB,,,CJPL,OVRHD & REG ,,B7 & SHIFT & SIGN
INR B8
OVRHD:ALU RAMQD,OR,ZB & REG ,,B7 & SHIFT
ALU RAMQD,OR,ZB & REG ,,B7 & SHIFT
ALU QREG,OR,ZA & REG R5
ALU NOP,ADD,DQ & REG R0 & FILEN & LDADR & BULKM CMD5
ALU NOP,ADD,ZA,1 & REG R7 & LDADR & BULKM CMD6
ALU NOP,OR,ZA & REG R8 & LDX & BUSRQ
ALU NOP,OR,ZA & REG R7 & LDADR & BUSRQ
ALU NOP,OR,DZ & LDZ & ZEN & LDAY & BUSRQ
ALU NOP,ADD,DQ & REG R1 & FILEN & LDML & LDADR
ALU RAMF,OR,DZ & REG ,,B6 & SFTEN & SHIFT & LDML
ALU NOP,OR,DZ & LDZ & ZEN & LDAY & BULKM CMD4
ALU NOP,SUBS,DA & REG R8 & LDX & BUSRQ
ALU NOP,ADD,ZA & REG A7,0 & LDML & LDADR & OCTRL CMD1
ALU NOP,ADD,DA & REG R6 & SFTEN & SHIFT & ZDBUS
ALU NOP,OR,DZ & ZEN & LDAY & BUSRQ
LDML & CONT
ALU RAMF,OR,DZ & REG ,,B6 & SFTEN & SHIFT
ALU NOP,OR,DZ & LDZ & ZEN & LDY
ALU NOP,OR,ZA & REG A8 & LDX
LDML & OCTRL CMD2 & CONT
ALU NOP,ADD,DA & REG R6 & LDD & ZDBUS & SFTEN & SHIFT
NEAR:ALU NOP,SUBR,DA,,,D#35 & REG R4
ALU RAMF,SUBR,ZB,,CJPL NEWEL & REG ,,B4 & SIGN 0
OUTH:
; SUBROUTINE TO SET THE OUTPUT SCAN LINE TO ZERO
ZSCAN:ALU NOP,AND,ZQ,,LDCTR,D#512 & LDD
LDI B9,D#1023
LDI B10,D#511
REPET:ALU NOP,OR,ZA & REG R9 & LDADR & OCTRL CMD1
ALU RAMA,SUBR,ZB & REG R10,,B9 & BUSRQ & DEN & OCTRL CMD1
ALU RAMF,SUBR,ZB,,RPCTR,REPET & REG ,,B10 & BUSRQ & DEN
CRTN & GND
END
```

What is claimed is:

1. Apparatus for providing multiple cardiac sector image displays comprising:

input controller means connected to receive input ultrasonic echo data representing cardiac sector images of a patient occurring during one or more cardiac cycles for digitizing in real time selected ones of said images thereby representing said images in a digital format, front panel interface means for specifying said selected ones of said images occurring during one of said cardiac cycles, storage means for storing in real time the digitized data, microprocessor means for controlling in real time the digitizing and storing of said input data and for enhancing said digital images, said microprocessor means including memory means for storing a predetermined program of instructions, means responsive to a first portion of said stored program for digitizing and storing said input data, means responsive to a second portion of said stored program for enhancing said digital images, and means responsive to a third portion of said stored program for converting said enhanced data into a format corresponding to an analog format, output controller means connected to receive the converted enhanced data for converting said enhanced data to an analog format for display, and analog strip chart recorder means connected to receive the enhanced data in said analog format for displaying said multiple sector images thereby representing a cardiac image profile.

2. Apparatus for providing multiple cardiac sector image displays comprising:

input controller means connected to receive input ultrasonic echo data representing cardiac sector images of a patient occurring during one or more cardiac cycles for digitizing in real time selected ones of said images thereby representing said images in a digital format, front panel interface means for specifying selected ones of said sector images occurring relative to a physiological event of the patent, storage means for storing in real time the digitized data, microprocessor means for controlling in real time the digitizing and storing of said input data and for enhancing said digital images, said microprocessor means including memory means for storing a predetermined program of instructions, means responsive to a first portion of said stored program for digitizing and storing said input data, means responsive to a second portion of said stored program for enhancing said digital images, and means responsive to a third portion of said stored program for converting said enhanced data into a format suitable for display, and digital recorder means connected to receive the converted enhanced data for displaying said multiple sector images thereby representing a cardiac image profile.

3. Apparatus for providing multiple cardiac sector image displays together with a patient's physiological parameters comprising:

input controller means connected to receive input ultrasonic echo data representing sector images having a number of scan lines where the images occur as elements on said scan lines and connected to receive other input data representing physiological parameters of a patient occurring during one or more cardiac cycles for digitizing in real time selected ones of said images thereby representing said images in a digital format, front panel interface means for specifying said selected ones of said sector images occurring relative to a physiological event of the patient, storage means for storing in real time the digitized data, microprocessor means for controlling in real time the digitizing and storage of said input data and for enhancing the digitized images, said microprocessor means including memory means for storing a predetermined program of instructions, means responsive to a first portion of said stored program for digitizing and storing said selected ones of said images and said other input data, means responsive to a second portion of said stored program for enhancing said digitized images without said scan lines, and means responsive to a third portion of said stored program for converting said enhanced data into a format suitable for display, monitor means connected to receive the converted enhanced images for displaying selected ones of said enhanced images thereby allowing previewing of said enhanced images, means for specifying selected ones of said enhanced images on said monitor means, and recorder means for displaying in hard copy form said selected enhanced images without said scan lines and for displaying said physiological parameters.

4. Apparatus for continuously refreshing a strobed frame on a cathode ray tube display comprising:

input controller means connected to receive input ultrasonic echo data representing cardiac sector images occurring during one or more cardiac cycles for digitizing in real time selected frames of said sector images where each of said frames occurs as one of said sector images thereby representing said images in a digitized format, means for specifying one of said frames each cardiac cycle as an operator-controlled variable time delay after an identifiable physiological event thereby forming a strobed frame, storage means for storing in real time said strobed frame each cardiac cycle such that each strobed frame is stored in the section of memory containing the previously strobed frame, monitor means for displaying the last stored strobed frame refreshed sufficiently often so as to avoid noticeable flicker, and microprocessor means for controlling the digitizing, storing and refreshing of said strobed images, said microprocessor means inlcuding memory means for storing a predetermined program of instructions, means responsive to a first portion of said stored program for digitizing and storing said input data, means responsive to a second portion of said stored program for enhancing said strobed frames, and means responsive to a third portion of said stored program for refreshing said strobed images.

5. Apparatus for providing multiple sector image displays comprising:

input controller means connected to receive input ultrasonic echo data representing sector images of a patient occurring during one or more cardiac cycles for digitizing in real time selected frames of said sector images where each of said frames occurs as one of said sector images thereby representing said images in a digital format, front panel interface means for specifying the storage of a cluster of said frames, storage means for storing in real time a plurality of frames of data where each new frame is stored in the memory area previously holding the oldest form of data, thereby forming a cluster of stored frames, microprocessor means for controlling in real time the digitizing and storing of said input data, and for enhancing said digital images, said microprocessor means including memory means for storing a predetermined program of instructions, means responsive to a first portion of said stored program for digitizing and storing said input data, means responsive to a second portion of said stored program for enhancing said digital images, control means for stopping the storage of new frames thereby freezing a cluster of frames occurring within a predetermined interval of time, monitor means for displaying one of the clustered frames, and means for selecting one or more of said stored and enhanced frames displayed on said monitor means to be output in hard copy form.

6. Apparatus for providing multiple sector image displays comprising:

input controller means connected to receive input ultrasonic echo data representing a patient's cardiac sector images occurring during one or more cardiac cycles for digitizing in real time selected frames of said sector images where each of said frames occurs as one of said sector images thereby representing said images in a digital format, means for strobing selected ones of said frames during said cardiac cycles based on a variable delay after an identifiable physiological event, storage means for storing in real time each strobed frame and for storing in real time a cluster of frames around said strobed frame, microprocessor means for controlling in real time the digitizing and storing of said input data and for enhancing said digital images, said microprocessor means including memory means for storing a predetermined program of instructions, means responsive to a first portion of said stored program for digitizing and storing said input data, means responsive to a second portion of said stored program for controlling the strobing of said selected ones of said frames, means responsive to a third portion of said stored program for controlling the stopping of the storage of said new clusters, and means responsive to a fourth portion of said stored program for enhancing said digital images, control means for stopping the storage of new clusters thereby freezing a cluster of frames ocurring within a period of time including the occurrence of the strobed frame, monitor means for displaying selected ones of said cluster of frames in soft copy form, and recorder means for recording selected ones of said enhanced frames in hard copy form.

7. Apparatus for providing multiple cardiac sector image displays comprising:

input controller means connected to receive input ultrasonic echo data representing cardiac sector images of a patient occurring during one or more cardiac cycles for digitizing in real time selected ones of said images thereby representing said images in a digital format, front panel interface means for specifying said selected ones of said images, means for strobing in real time selected ones of said frames during said cardiac cycles based on a variable delay after the R-wave of an electrocardiogram, storage means for storing in real time each strobed frame once each cardiac cycle such that each new strobed frame is stored in the section of memory previously containing the oldest strobed frame, control means for stopping the storage of new sectors, thereby freezing the last several strobed frames in memory, microprocessor means for controlling in real time the digitizing and storing of said input data and enhancing said digital images, said microprocessor means including memory means for storing a predetermined program of instructions, means responsive to a first portion of said stored program for digitizing and storing said input data, means responsive to a second portion of said stored program for controlling the strobing of said selected ones of said frames, means responsive to a third portion of said stored program for controlling the displaying of said images, and means responsive to a fourth portion of said stored program for controlling the display of said selected enhanced images, monitor means connected to receive said input data for displaying said images in soft copy form thereby permitting previewing of said images, and means for displaying the selected enhanced images in hard copy form.

8. Apparatus for providing multiple sector image displays comprising:

input controller means connected to receive input
ultrasonic echo data in polar coordinates representing sector images of a patient for digitizing in real time selected frames of said sector images thereby representing said images in a digital format, front panel interface means for specifying said selected frames, storage means for storing in real time said selected frames, monitor means connected to display said input data representing sector images, means for specifying selected ones of said displayed frames, microprocessor means for controlling in real time the digitizing and storing of said input data, for enhancing said digital images, and for converting in real time said polar coordinates to rectangular coordinates, said microprocessor means including memory means for storing a predetermined program of instructions, means responsive to a first portion of said stored program for digitizing and storing of said input data, means responsive to a second portion of said stored program for enhancing said digital images, means responsive to a third portion of said stored program for converting said polar coordinates to rectangular coordinates, and recorder means connected to receive the converted enhanced data for displaying said selected enhanced images in hard copy form.

9. Apparatus for providing multiple sector image displays comprising:

input controller means connected to receive input ultrasonic echo data in polar coordinates representing sector images of a patient for digitizing in real time selected frames of said sector images thereby representing said images in a digital format, front panel interface means for specifying said selected frames, storage means for storing in real time said selected frames, monitor means connected to display said input data representing sector images, means for specifying selected ones of said displayed frames, microprocessor means for controlling in real time the digitizing and storing of said input data, for enhancing said digital images, and for converting in real time said polar coordinates to rectangular coordinates, said microprocessor means including memory means for storing a predetermined program of instructions, means responsive to a first portion of said stored program for digitizing and storing of said input data, means responsive to a second portion of said stored program for enhancing said digital images, and means responsive to a third portion of said stored program for converting said polar coordinates to rectangular coordinates, and means responsive to a fourth portion of said stored program for controlling the display of said enhanced data, and M-mode video strip chart recorder means connected to receive the enhanced data for displaying said selected enhanced images in hard copy form on the same recorder means that is utilized for M-mode recordings.

10. Apparatus for providing one or more sector image displays comprising:

input controller means connected to receive input ultrasonic echo data in two dimensional format representing one or more sector images for digitizing in real time selected frames of said sector images where each of said frames occurs as one of said sector images thereby representing said images in a digitized format, monitor means connected to receive said input data for displaying said sector images in soft copy form thereby allowing previewing of said images, front panel interface means for specifying said selected frames, storage means for storing in real time said selected frames by row and column corresponding to said two dimensional format thereby eliminating the need for processing time to compute addresses for a conventional one dimensional memory when processing two dimensional data, microprocessor means for controlling in real time the digitizing of said input data, for storing and accessing in real time said input data by row and column and for enhancing said digital images, said microprocessor means including memory means for storing a predetermined program of instructions, means responsive to a first portion of said stored program for digitizing of said input data, means responsive to a second portion of said stored program for storing and accessing of said input data by row and column, means responsive to a third portion of said stored program for enhancing of said digitial images, means responsive to a fourth portion of said stored program for controlling the display of said sector images, and display means connected to receive said selected frames for displaying said multiple sector images.

11. Apparatus for providing high-resolution abdominal sector image displays comprising:

input controller means connected to receive input ultrasonic echo data in polar coordinates representing sector images having a number of scan lines for digitizing selected images thereby representing said images in a digital format, storage means for storing in real time at least one frame of the digitized data, microprocessor means for controlling in real time the digitizing and storing of said input data and for improving the resolution of the data through deconvolution processing, and for converting in real time the data from said polar coordinates to rectangular coordinates, and for interpolating in real time between data points so that the original scan lines are not apparent in the output format, said microprocessor means including memory means for storing a predetermined program of instructions, means responsive to a first portion of said stored program for digitizing and storing of said input data, means responsive to a second portion of said stored program improving the resolution of said input data through deconvolution processing, means responsive to a third portion of said stored program for converting said polar coordinates to rectangular coordinates, means responsive to a fourth portion of said stored program for interpolating between data points so that the original scan lines are not apparent in the output format, and recorder means connected to receive the processed data for displaying said processed data in hard copy form.

12. Apparatus for providing multiple sector image displays comprising:

input controller means connected to receive input ultrasonic echo data representing sector images having a number of scan lines where the images occur as elements on said scan lines for digitizing in real time selected ones of said images thereby representing said images in a digital format, front panel interface means for specifying said selected ones of said sector images, storage means for storing in real time the digitized elements, microprocessor means for controlling in real time the digitizing and storage of said input data and for generating in real time a number of elements, greater then the number of the stored elements by interpolating between said stored elements thereby eliminating spaces between said scan lines and enhancing the digitized images, said microprocessor means including memory means for storing a predetermined program of instructions, means responsive to a first portion of said stored program for digitizing and storing of said input data, means responsive to a second portion of said stored program for controlling the generation of said number of elements, and means responsive to a third portion of said stored program for controlling the display of said selected enhanced images, and recorder means for displaying in hard copy form said selected enhanced images.

13. Apparatus for providing one or more sector image displays comprising:

input controller means connected to receive input data representing ultrasonic echo sector images of a patient for digitizing in real dime selected frames of said sector images where each of said frames occurs as one of said sector images thereby representing said images in a digital format, front panel interface means for specifying said selected ones of said sector frames, storage means for storing in real time the digitized sector data in rows corresponding to echoes from a single direction where adjacent rows of sector data correspond to sector data from different directions with angular increments from row to row, thereby forming a number of columns of data representing all of the data from a single depth into the tissue, microprocessor means for controlling in real time the digitizing and storing of said input data for selecting data from said columns where each column represents sector data from a single depth of scanning, for deconvolving each column of data thereby enhancing the data, and for writing the enhanced data into said storage means, said microprocessor means including memory means for storing a predetermined program of instructions, means responsive to a first portion of said stored program for digitizing and storing of said input data, means responsive to a second portion of said stored program for selecting data from said columns, means responsive to a third portion of said stored program for deconvolving each column, and means responsive to a fourth portion of said stored program for writing said enhanced data, and recorder means connected to receive said selected frames for displaying said enhanced images.

14. Apparatus for providing one or more sector image displays comprising:

input controller means connected to receive input ultrasonic echo data representing sector frames having a first number of scan lines where the frames occur as elements on said scan lines for digitizing in real time selected ones of said frames thereby representing said frames in a digital format, front panel interface means for specifying said selected ones of said sector frames, storage means for storing in real time the digitized data, microprocessor means for controlling in real time the digitizing and storage of said input data, for enhancing the digitized frames thereby forming an enhanced sector image for each of said sector frames, where each of said frames includes a number of scan lines corresponding to said first number, and for refreshing said scan lines on monitor means faster than in real time so that the entire frame of stored data can be written on the monitor means at least twice during the time taken to acquire the data in real time by interleaving successive refreshes of the frame of data on the monitor means thereby reducing spaces between the stored scan lines, said microprocessor means including memory means for storing a predetermined program of instructions, means responsive to a first portion of said stored program for digitizing and storing of said input data, means responsive to a second portion of said stored program for enhancing said digitized frames, means responsive to a third portion of said stored program for refreshing said scan lines on said monitor means faster than in real time, means responsive to a fourth portion of said stored program for controlling the display of said selected enhanced images, and monitor means for displaying the selected enhanced images.

15. Apparatus for providing multiple cardiac sector image displays comprising:

input controller means connected to receive input ultrasonic echo data representing cardiac sector images of a patient occurring during one or more cardiac cycles for digitizing in real time selected frames of said sector images where each of said frames occurs as one of said sector images thereby representing said images in a digital format, means for specifying said selected frames, storage means for storing in real time said selected frames each cardiac cycle, microprocessor means for controlling in real time the digitizing and storing of said input data and for enhancing said digital images, said microprocessor means including memory means for storing a predetermined program of instructions, means responsive to a first portion of said stored program for digitizing and storing of said selected frames, means responsive to a second portion of said stored program for enhancing said selected digital images, means responsive to a third portion of said stored program for controlling the display of said enhanced images, means responsive to a fourth portion of said stored program for controlling the cyclic display of said enhanced images, monitor means for displaying said enhanced images, and cycle switch means for cycling sequentially the stored enhanced images on said monitor means thereby representing a cardiac cycle.

* * * * *